United States Patent
Islam et al.

(10) Patent No.: US 12,089,945 B2
(45) Date of Patent: *Sep. 17, 2024

(54) ORGAN OR TISSUE HEMODYNAMIC AND METABOLIC FUNCTION MEASURED USING SUPER-CONTINUUM LIGHT SOURCES

(71) Applicant: THE REGENTS OF THE UNIVERSITY OF MICHIGAN, Ann Arbor, MI (US)

(72) Inventors: Mohammed N. Islam, Ann Arbor, MI (US); Steven P. Broglio, Ann Arbor, MI (US); Ioulia Kovelman, Ann Arbor, MI (US); Hasan Alam, Ann Arbor, MI (US); Rachel M. Russo, Ann Arbor, MI (US); Alexander Joseph Rogers, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/990,550

(22) Filed: Nov. 18, 2022

(65) Prior Publication Data
US 2023/0093350 A1 Mar. 23, 2023

Related U.S. Application Data

(63) Continuation of application No. 17/164,490, filed on Feb. 1, 2021, now Pat. No. 11,529,091.
(Continued)

(51) Int. Cl.
*A61B 5/1455* (2006.01)
*A61B 5/00* (2006.01)
(Continued)

(52) U.S. Cl.
CPC ........ *A61B 5/4064* (2013.01); *A61B 5/14546* (2013.01); *A61B 5/14552* (2013.01);
(Continued)

(58) Field of Classification Search
CPC . A61B 5/4064; A61B 5/14546; A61B 5/1455; A61B 5/14552; A61B 5/4866;
(Continued)

(56) References Cited

U.S. PATENT DOCUMENTS 7,330,745 B2  2/2008  Kawasaki et al.
7,353,054 B2  4/2008  Kawasaki et al.
(Continued)

OTHER PUBLICATIONS

Arredondo, M. M., Hu, X. S., Satterfield, T., & Kovelman, I., "Bilingualism alters childrens frontal lobe functioning for attentional control," Developmental science, 20(3), e12377 (2017).
(Continued)

*Primary Examiner* — Eric F Winakur

(57) ABSTRACT

An apparatus is described for measuring hemodynamic or metabolic function of an organ or tissue region of a subject comprising a super-continuum laser operating in the near or short-wave infrared wavelength range and comprising a multi-stage amplifier. A source fiber delivers the super-continuum emission to the organ or tissue region, and a collection fiber receives reflected emission from the region. A detector followed by a processor is used to determine a metabolic state and an oxygenation state of the organ or tissue region. A signal-to-noise ratio of the signal is improved using a dual-arm differential measurement technique.

20 Claims, 21 Drawing Sheets

Related U.S. Application Data

(60) Provisional application No. 62/968,736, filed on Jan. 31, 2020.

(51) Int. Cl.
*A61B 5/145* (2006.01)
*A61B 90/30* (2016.01)

(52) U.S. Cl.
CPC .......... *A61B 5/4866* (2013.01); *A61B 5/7246* (2013.01); *A61B 5/7278* (2013.01); *A61B 5/7282* (2013.01); *A61B 2090/306* (2016.02); *A61B 2562/0238* (2013.01)

(58) Field of Classification Search
CPC .... A61B 5/7246; A61B 5/7278; A61B 5/7282
See application file for complete search history.

(56) References Cited

U.S. PATENT DOCUMENTS

| | | |
|---|---|---|
| 2010/0234837 A1 | 9/2010 | Alfano |
| 2016/0035093 A1 | 2/2016 | Kateb et al. |
| 2018/0286044 A1 | 10/2018 | Boppart et al. |
| 2018/0325449 A1 | 11/2018 | Bentz et al. |
| 2021/0080382 A1 | 3/2021 | Alfano et al. |
| 2021/0321915 A1 | 10/2021 | Barbour et al. |

OTHER PUBLICATIONS

Arredondo, M. M., Hu, X. S., Satterfield, T., Riobóo, A. T., Gelman, S. A., & Kovelman, I., "Bilingual effects on lexical selection: A neurodevelopmental perspective," Brain and Language, 195, 104640 (2019).

Bale, G., Elwell, C. E., & Tachtsidis, I., "From Jöbsis to the present day: a review of clinical near-infrared spectroscopy measurements of cerebral cytochrome-c-oxidase," Journal of biomedical optics, 21(9), 091307 (2016).

Bale, G., Mitra, S., Meek, J., Robertson, N., & Tachtsidis, I, "A new broadband near-infrared spectroscopy system for in-vivo measurements of cerebral cytochrome-c-oxidase changes in neonatal brain injury," Biomedical optics express, 5(10), 3450-3466 (2014).

Bazil, J. N., Beard, D. A., & Vinnakota, K. C., "Catalytic coupling of oxidative phosphorylation, ATP demand, and reactive oxygen species generation," Biophysical journal, 110(4), 962-971 (2016).

Brunori, M., Antonini, E., & Wilson, M. T., "Cytochrome c oxidase: an overview of recent work," Metal ions in biological systems, 13, 188-228 (1981).

Duncan, A., Meek, J. H., Clemence, M., Elwell, C. E., Tyszczuk, L., Cope, M., & Delpy, D., "Optical pathlength measurements on adult head, calf and forearm and the head of the newborn infant using phase resolved optical spectroscopy," Physics in Medicine & Biology, 40(2), 295 (1995).

Emir, U. E., Ozturk, C., & Akin, A., "Multimodal investigation of fMRI and fNIRS derived breath hold Bold signals with an expanded balloon model," Physiological measurement, 29(1), 49 (2007).

Greenwood, C., Wilson, M. T., & Brunori, M., "Studies on partially reduced mammalian cytochrome oxidase. Reactions with carbon monoxide and oxygen," Biochemical Journal, 137(2), 205-215 (1974).

Huppert, T. J., Diamond, S. G., Franceschini, M. A., & Boas, D. A., "HomER: a review of time-series analysis methods for near-infrared spectroscopy of the brain," Applied optics, 48(10), D280-D298 (2009).

Islam, M. N., "Infrared Super-continuum Light Sources and Their Applications," in [*Raman Fiber Lasers*], Springer, Cham, 117-203 (2017).

Jones, G. D., Jones, M. G., Wilson, M. T., Brunori, M., Colosimo, A., & Sarti, P., "Reactions of cytochrome c oxidase with sodium dithionite," *Biochemical Journal*, 209(1), 175-182 (1983).

Kolyva, C., Tachtsidis, I., Ghosh, A., Moroz, T., Cooper, C. E., Smith, M., & Elwell, C. E., "Systematic investigation of changes in oxidized cerebral cytochrome c oxidase concentration during frontal lobe activation in healthy adults," Biomedical optics express, 3(10), 2550-2566 (2012).

Lange, F., Dunne, L., Hale, L., & Tachtsidis, I., "Maestros: a multiwavelength time-domain NIRS system to monitor changes in oxygenation and oxidation state of Cytochrome-C-Oxidase," IEEE Journal of Selected Topics in Quantum Electronics, 25(1), 1-12 (2018).

Matcher, S. J., Elwell, C. E., Cooper, C. E., Cope, M., & Delpy, D. T., "Performance comparison of several published tissue near-infrared spectroscopy algorithms," *Analytical biochemistry*, 227(1), 54-68 (1995).

Siddiqui, M. F., Lloyd-Fox, S., Kaynezhad, P., Tachtsidis, I., Johnson, M. H., & Elwell, C. E., "Non-invasive measurement of a metabolic marker of infant brain function," Scientific reports, 7(1), 1330 (2017).

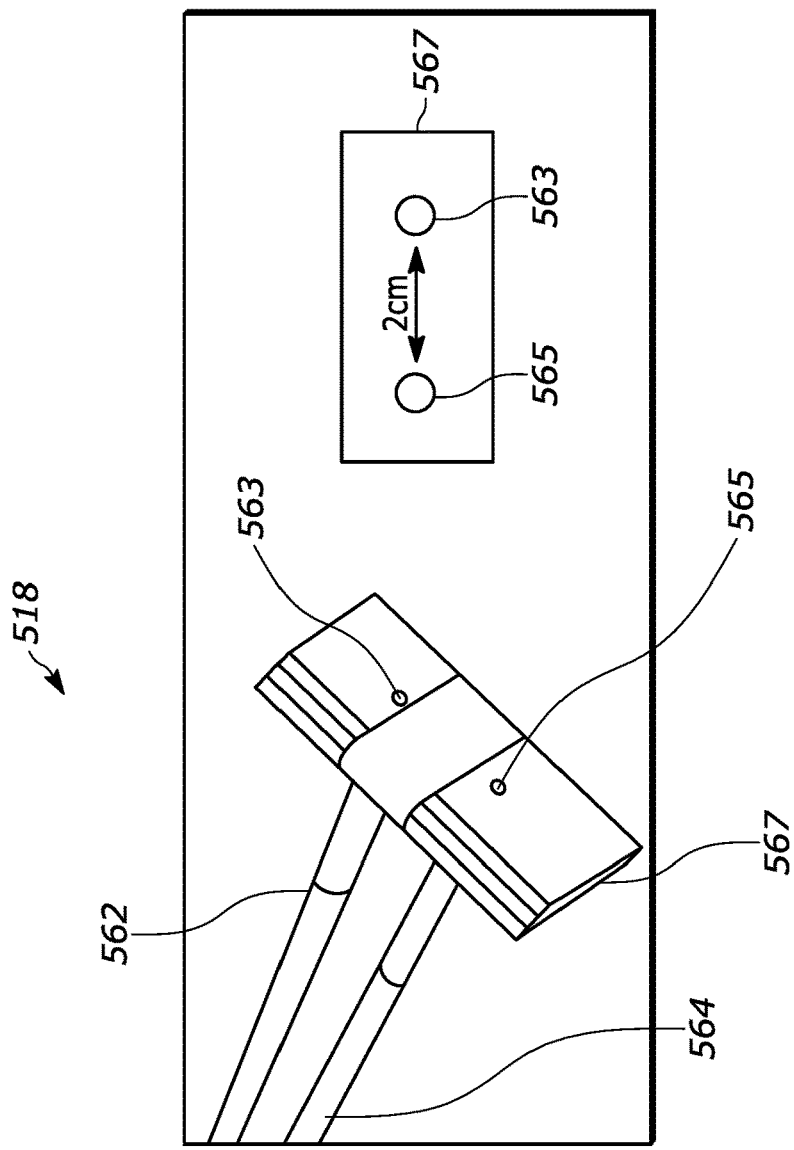
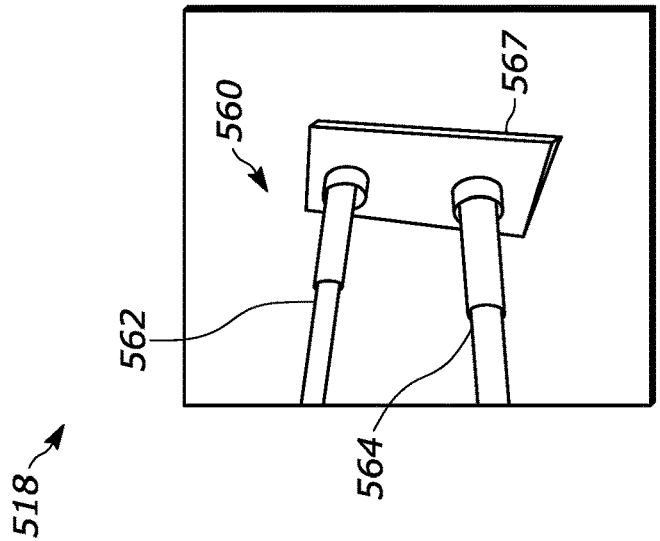
FIG. 5C
FIG. 5B

| SUBJECT # | CCO DECREASING COUNTS FOR BEST 6 |
|---|---|
| 1 | 4 |
| 2 | 3 |
| 3 | 3 |
| 4 | 3 |
| 5 | 5 |
| 6 | 2 |
| 7 | 6 |
| 10 | 3 |
| 12 | 5 |
| 13 | 5 |
| 15 | 3 |
| 16 | 4 |
| 17 | 4 |
| 18 | 4 |
| 19 | 4 |
| 20 | 4 |
| 23 | 6 |
| SUM | 68 (66.7%) |

| SUBJECT # | HbO INCREASING COUNTS | CCO DECREASING COUNTS |
|---|---|---|
| 1 | 3 | 2 |
| 2 | 5 | 3 |
| 3 | 5 | 3 |
| 4 | 2 | 2 |
| 5 | 6 | 5 |
| 6 | 2 | 2 |
| 7 | 6 | 6 |
| 10 | 2 | 2 |
| 12 | 7 | 6 |
| 13 | 4 | 4 |
| 15 | 4 | 3 |
| 16 | 4 | 3 |
| 17 | 6 | 4 |
| 18 | 5 | 3 |
| 19 | 4 | 3 |
| 20 | 4 | 3 |
| 23 | 3 | 3 |
| SUM | 72 (47% OF TOTAL BLOCKS) | 57 (79.2%) |

FIG. 18

ORGAN OR TISSUE HEMODYNAMIC AND METABOLIC FUNCTION MEASURED USING SUPER-CONTINUUM LIGHT SOURCES

CROSS-REFERENCE TO RELATED APPLICATION

This application is a continuation of U.S. application Ser. No. 17/164,490, filed Feb. 1, 2021, which claims the benefit of U.S. Provisional Patent Application No. 62/968,736, filed Jan. 31, 2020. The entire disclosures of these applications are hereby incorporated by reference herein in their entireties.

FIELD OF THE INVENTION

The disclosure relates generally to methods for measuring the metabolic tissue state of a subject, and more particularly to super-continuum optical methods for measuring markers of cell function.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Much of what we know about human brain function today, in health and in disease, is offered through the lens of tissue oxygenation. Oxygen is necessary for cellular metabolism and, thus, changes in the flow of oxygenated blood to areas of the brain may reflect a change in underlying neural activity.

Numerous techniques have been used to measure oxygen for assessing brain function. Functional Magnetic Resonance (fMRI) uses magnetic fields to non-invasively assess the flow of oxygenated/deoxygenated hemoglobin within cerebral blood vessels, also known as the BOLD signal, an established correlate of regional brain activity. In other examples, optical methods, such as functional Near Infrared Spectroscopy (fNIRS), have been used to measure changes in the oxidation state of hemoglobin by capturing subtle changes in the color properties of red blood cells. Among the advantages of these later examples, optical imaging devices are silent, compact, portable, and do not interfere with other medical devices, which makes them an ideal bed-side complement to fMRI and even computerized tomography scans.

Nevertheless, these conventional oxygen measurement techniques are limited. A core limitation of hemodynamic neuroimaging systems, for example, is that they capture changes in blood flow to the brain, but not the changes in the neural tissue itself. This limitation is of particular importance in the presence of illness or injury, when brain tissue dysfunction may occur without alteration in regional hemodynamics.

As such, there has been interest in measuring optically active markers of cellular function, such as Cytochrome. Cytochrome is a protein internal to the neuron's mitochondria that changes form during neuron's internal metabolic activity. By capturing changes in Cytochrome-C-Oxidase (CCO), it is believed that one can measure neural metabolism to aid in the diagnosis and management of neurological injury or illness. CCO, in particular, is a photo-sensitive enzyme that reacts with oxygen in the last step of mitochondrial electron transport chain. In the electron transport chain, protons are moved across the mitochondrial inner membrane to produce of adenosine triphosphate (ATP), the energy source used for cells to live and function. CCO exists in two states: oxidized CCO and reduced CCO. The sum of these two CCO states is a constant. The ratio of oxidized CCO to reduced CCO is termed the redox state and can be detected by its spectroscopic signal. Increased cellular activity uses more energy in the form of ATP. This increase in ATP utilization results in the conversion of oxidized CCO to reduced CCO, which equates to a reduction of the redox state of CCO and a decrease in the spectroscopic signal. Thus, a reduction in ATP synthesis, such as occurs when the substrates for ATP generation (oxygen and blood flow) are reduced from ischemic or hypoxic insults induced by illness or injury, would be reflected by changes in CCO redox state.

CCO is responsible for more than 95% of oxygen metabolism in the body and is very important for the efficient generation of ATP. Thus, if effective techniques were available for measuring CCO, that measurement could add key precision in understanding of brain cellular function. Moreover, simultaneous measurements of CCO and hemoglobin redox states could provide complimentary information on the brain's metabolism and hemodynamics, information that could improve the diagnosis and management of neuronal illness or injury. CCO concentration is also significantly higher in the brain than in extra-cerebral tissues. As such, there is minimal spectral interference from the scalp and skull when brain tissue is assessed non-invasively. Therefore, non-invasive spectroscopic assessment of CCO and hemoglobin redox states has the potential to significantly enhance many areas of clinical practice.

Yet, despite the attractiveness of CCO as a metabolic marker, measuring CCO is difficult for a number of reasons. First, the in vivo concentration of CCO is between 5% to 10% that of hemoglobin, which makes CCO very hard to detect relative to hemoglobin at a particular location. Further, because CCO and hemoglobin have overlapping spectra, there can be significant cross-talk between CCO changes and the hemodynamic response. Also, CCO is an enzyme with four redox centers, one of which—copper A—has a broad absorption peak in the near-infrared (NIR) spectrum between 700-900 nm that changes depending on its redox state. The relatively broad, featureless spectrum for the redox state of CCO makes it more difficult to distinguish from other interfering spectra. Some have proposed using conventional super-continuum light sources (SCL) to provide high brightness sources with the hopes of measuring CCO with enhanced signal-to-noise ratio. However, these conventional systems are plagued with generally poor signal-to-noise ratio (SNR). For example, Kolyva and colleagues' (Kolyva, C., Tachtsidis, I., Ghosh, A., Moroz, T., Cooper, C. E., Smith, M., & Elwell, C. E., "Systematic investigation of changes in oxidized cerebral cytochrome c oxidase concentration during frontal lobe activation in healthy adults," Biomedical optics express, 3(10), 2550-2566 (2012)) non-invasive human cognitive testing uses a lamp or black body radiator as a light source, which provides low light brightness resulting in poor SNR and measurement contrast. Lange and colleagues (Lange, F., Dunne, L., Hale, L., & Tachtsidis, I., "MAESTROS: a multiwavelength time-domain NIRS system to monitor changes in oxygenation and oxidation state of Cytochrome-C-Oxidase," IEEE Journal of Selected Topics in Quantum Electronics, 25(1), 1-12 (2018)) use a mode-locked laser based super-continuum light source, but they only applied their device to physiological measurements on forearm muscles. Therefore, they were unable to see any significant CCO changes.

Thus, there is a need for a highly accurate, broad spectrum, high signal-to-noise ratio techniques to permit measurement of CCO from which healthcare professionals can distinguish CCO from the hemodynamic response, skin interference, and motion artifacts, for diagnostic purposes. Moreover, there is a need for techniques for monitoring of concussion, brain function, organ condition and other medical applications, using non-invasive method of monitoring tissue metabolism, through CCO measurement and determination of correlations and dis-correlations to oxygenation.

SUMMARY OF THE INVENTION

In one embodiment, an apparatus is disclosed for measuring hemodynamic or metabolic function of an organ or tissue region of a subject, the apparatus comprising a super-continuum laser configured to generate a pulsed super-continuum emission, the emission having a wavelength range coinciding with at least one of a near infrared (NIR) wavelength range and a short-wave infrared (SWIR) wavelength range. The fiber super-continuum laser includes a multi-stage configuration formed of a fiber pre-amplifier stage feeding an optical noise filtering stage feeding a fiber amplifier stage generating the pulsed super-continuum emission. A probe having a probe housing fixedly connected to a source fiber is configured to receive the pulsed super-continuum emission from the fiber amplifier stage, the probe housing further fixedly connected to a collection fiber configured to receive reflected emission from the organ or tissue region. The probe is configured to apply via the source fiber the super-continuum emission to the organ or tissue region of the subject, and the probe further is configured to receive the reflected emission from the organ or tissue region via the collection fiber. A detector is configured to detect the reflected emission and is further configured to generate a signal indicative of the detected reflected emission. A processor is configured to execute machine readable instructions that, when executed, cause the processor to determine, from the signal indicative of the reflected emission, a simultaneous (i) metabolic state of the organ or tissue region from a metabolic chromophore and (ii) an oxygenation state of the organ or tissue region from at least one oxygenation chromophore. Moreover, a signal-to-noise ratio of the signal is improved by using a dual-arm differential measurement technique including a beam splitter configured to separate the pulsed super-continuum emission to generate a sample arm beam and a reference arm beam, wherein the sample arm beam is provided to the probe and the reference arm beam is provided to a reference detector configured to generate another signal indicative of the detected reference arm beam. The signal-to-noise ratio is further improved using a lock-in technique or a polarizer, and wherein the machine readable instructions further cause the processor to compare the data of the another signal indicative of the reference arm beam with the signal indicative of the reflected emission to identify an organ or tissue functionality.

In another embodiment, an apparatus is disclosed for measuring hemodynamic or metabolic function of an organ or tissue region of a subject, the apparatus comprising a super-continuum laser configured to generate a pulsed super-continuum emission. The emission has a wavelength range coinciding with at least one of a near infrared (NIR) wavelength range and a short-wave infrared (SWIR) wavelength range, and the fiber super-continuum laser has a multi-stage configuration formed of a fiber pre-amplifier stage feeding an optical noise filtering stage feeding a fiber amplifier stage generating the pulsed super-continuum emission. A probe having a probe housing fixedly connected to a source fiber is configured to receive the pulsed super-continuum emission from the fiber amplifier stage, the probe housing is further fixedly connected to a collection fiber configured to receive reflected emission from the organ or tissue region. The probe is configured to apply via the source fiber the super-continuum emission to the organ or tissue region of the subject, and the probe is further configured to receive the reflected emission from the organ or tissue region via the collection fiber. A detector is configured to detect the reflected emission and is further configured to generate a signal indicative of the detected reflected emission. A processor is configured to execute machine readable instructions that, when executed, cause the processor to determine, from the signal indicative of the reflected emission, a (i) metabolic state of the organ or tissue region from a metabolic chromophore or (ii) an oxygenation state of the organ or tissue region from at least one oxygenation chromophore. The processor identifies and provides an output indicative of an organ or tissue functionality.

In yet another embodiment, an apparatus is disclosed for measuring hemodynamic or metabolic function of one or more organ or tissue regions of a subject, the apparatus comprising a super-continuum laser configured to generate a pulsed super-continuum emission, the emission having a wavelength range coinciding with at least one of a near infrared (NIR) wavelength range and a short-wave infrared (SWIR) wavelength range. A probe has a probe housing fixedly connected to a source fiber bundle comprising a plurality of source fibers configured to receive the pulsed super-continuum emission from the super-continuum laser, and the probe housing is further coupled to a collection fiber bundle comprising a plurality of collection fibers configured to receive reflected emission from a tissue region. The probe is configured to apply via one or more of the source fibers the super-continuum emission to the one or more organ or tissue regions of the subject, wherein the one or more organ or tissue regions comprise a forehead, temple, scalp, forearm, leg, chest or another body part of the subject, and the probe is further configured to receive the reflected emission from the one or more organ or tissue regions via one or more of the collection fibers. One or more detectors are configured to detect the reflected emission and are further configured to generate one or more signals indicative of the detected reflected emission. A processor is included that is configured to execute machine readable instructions that, when executed, cause the processor to determine, from the one or more signals indicative of the detected reflected emission, a (i) metabolic state of the one or more organ or tissue regions from a metabolic chromophore and (ii) an oxygenation state of the one or more organ or tissue regions from at least one oxygenation chromophore. The processor also compares the metabolic state to a previous metabolic state of the one or more organ or tissue regions and determine, and from the comparison of the metabolic state and previous metabolic state, determines a trend of the metabolic state. The processor further compares the oxygenation state to a previous oxygenation state of the one or more organ or tissue regions and determines, from the comparison oxygenation state and the previous oxygenation state, a trend of the oxygenation state. The processor also determines a correlation between the trend of the metabolic state and the trend of the oxygenation state, and the processor identifies an organ or tissue functionality of the subject from the determined correlation.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 5B illustrates example probe ends of a fiber-based probe of the SCL system of FIG. 5A.

FIG. 5C illustrates example prove ends and geometries of a fiber-based probe of the SCL system of FIG. 5A.

FIG. 18 is a table illustrating the results of an "HbO increasing" filter on the data presented in FIG. 17.

DETAILED DESCRIPTION

Figure 1:
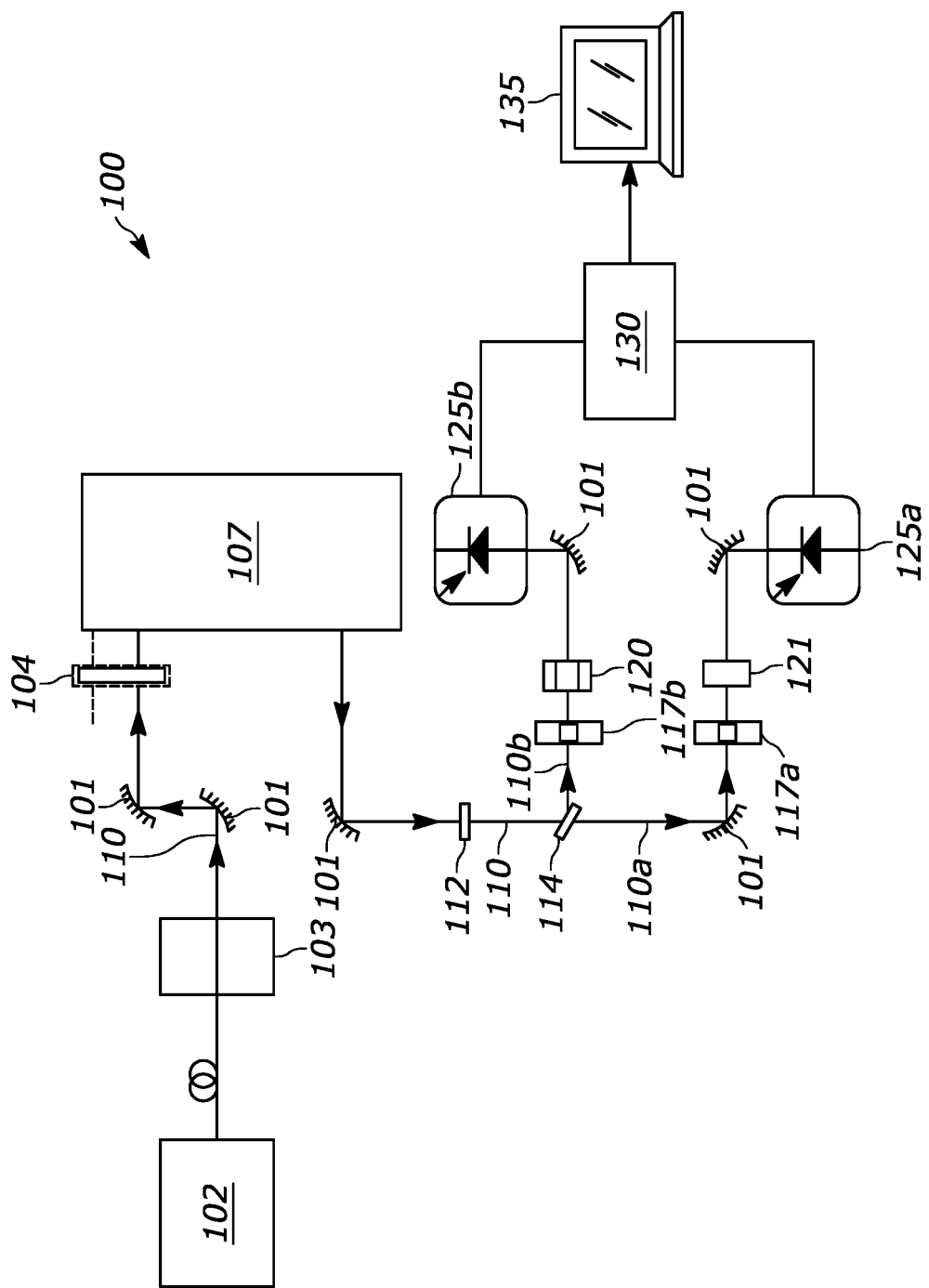
FIG. 1 is a block diagram of an example optical set-up for in vitro laboratory measurements of CCO and oxygenation.

The present application provides techniques for measuring metabolic tissue state and tissue oxygenation, through optical techniques capable of simultaneous measurement at single region of interest. In particular, the techniques measure Cytochrome-C-Oxidase (CCO), Cytochrome being a protein internal to the neuron's mitochondria that changes form during neuron's internal metabolic activity and thus is expressive of tissue metabolic condition. The techniques additionally include measuring oxygenation by measuring oxygenated hemoglobin (HbO) and deoxygenated (HbR) hemoglobin, which may be measured simultaneously with CCO. For example, in various examples herein, HbO and HbR are measured with CCO under different conditions for a subject and correlations and dis-correlations between CCO and either or both of HbO and HbR are measured. Capturing changes in CCO and oxygenation simultaneously and highly accurately, in particularly in and around the brain, enables the measurement of neural metabolism and allows the use of correlations/dis-correlations to oxygenation to aid in the diagnosis and management of neurological injury or illness. The ability to simultaneous measure metabolism and oxygenation and the ability to accurately assess correlations therebetween, offer numerous advantages over conventional techniques which measure metabolism and oxygenation separately. The described methods provide a means to distinguish CCO from the hemodynamic response, skin interference, and motion artifacts, for diagnostic purposes. This isolation of the CCO is particularly important at point of care, where traditional systems have been plagued within inaccuracies. The disclosed measurement techniques enable monitoring for conditions such as concussion, brain function, organ condition and other medical applications, using non-invasive methods.

In various examples, the present techniques provide for non-invasive interrogation of the redox state of the CCO enzyme as well as blood oxygenation, using a super-continuum laser infrared spectroscopy system that measures CCO (collectively referred to herein as the super-continuum laser (SCL) systems). The SCL systems, in some examples, use an all-fiber integrated, super-continuum light source that allows for substantial reduction in motion artifacts. In various examples, the SCL systems optically assay the redox state and also simultaneously measure HbO and HbR. Beyond providing hemodynamic and metabolism information simultaneously, these techniques can verify the fidelity of the measurements by comparing the hemoglobin measurements with more traditional instruments, such as commercially available fNIRS systems.

In various examples, the SCL systems described herein provide an order of magnitude improvement, or more, in brightness compared to tungsten-halogen lamps typically employed for CCO measurements. A considerable improvement in signal-to-noise ratio (SNR) over conventional systems allows for more accurate measurement of CCO and notably heretofore unable correlation measurements between CCO and HbO and HbR. Indeed, in various examples, the SCL systems can be enhanced for even greater SNR, by deploying a pulsed super-continuum laser source and a detection system synchronized to the pulsed super-continuum laser. For example, in some variations, the SCL systems include a SNR that can further obtain a ~30× improvement arising from time-gated detection of pulsed SCL light, and change detection (e.g., subtracting SCL on signals from SCL off signals) further improves the SNR by subtracting out background light.

In any event, the high brightness, fiber-delivery of example SCL systems as described herein facilitates clinical applications by accomplishing a deeper brain penetration and higher SNR, which help to distinguish CCO signal from clutter or interference from hemodynamic response, scalp and skull light scattering, and other chemicals in the brain. In particular examples herein, a SCL system configuration is demonstrated with a two-arm differential set-up with receivers, along with a quantification of the sensitivity and selectivity of CCO measurements. While the disclosed methods and systems are described in reference to monitoring and measurements of brain metabolism and functionality, the methods and systems described may be used to perform measurements of CCO, HbO, and HbR of any organ to determine the metabolic function, and potentially, normal and abnormal function of another organ. For example, the methods and systems described may be used to measure the metabolic function of a liver, kidney, heart, lungs, bladder, stomach, intestines, bowels, skin, muscles, or another organ of a human or an animal. Further, the system and methods described may be used in measuring and monitoring the metabolic function and normal/abnormal functionality of tissues such as muscle tissue, nervous tissue, and epithelial tissues. Therefore, the techniques described herein in reference to detection and monitoring of subject's brain also apply to detection and monitoring of other suitable organs of a subject.

The SCL systems and methods described may be used to aid in the early detection of brain injury/neuronal dysfunction and to monitor neuronal metabolism and cerebral oxygenation in response to on-going injury and/or therapy to guide treatments. The SCL measurement technologies disclosed provide information that allows clinicians to render treatments that protect tissue, improve neurologic function and speed recovery for brains, and other organs and tissues. Applications of the described SCL systems include any scenario having a risk of brain ischemia or injury or when it is otherwise difficult to use standard techniques including imaging, neurological exams, and other examination methods to determine functionality and metabolic function of an organ of tissue.

FIG. 1 is a block diagram of an example optical set-up 100 for in vitro laboratory measurements of CCO and oxygenation. In the illustrated example, the light source is an all-fiber integrated super-continuum laser (SCL) 102 that operates over the NIR and short-wave infrared (SWIR) wavelength range. As an example, the NIR can cover the wavelength range of approximately 700 nanometers to approximately 1000 nanometers, and the SWIR can cover the wavelength range of approximately 1000 nanometers to 2500 nanometers. The output of the SCL 102 is physically coupled to an XYZ stage 103 for alignment, to output a light beam 110 that is provided to a spectrometer 107 after passing through a chopper 104. In the illustration, mirrors 101 are used to guide the beam 110 throughout the optical set-up 100. In embodiments, the chopper 104 may be a rotating blade with blocking and non-blocking sections. The chopper 104 modulates the light beam 110 (e.g., by providing times during which the light is blocked and times during with the light is unblocked). Although a mechanical chopper is used in this embodiment, the chopper 104 may include one or more electro-optic modulators, acousto-optic modulators, free-space mechanical shutters, or MEMS-based beam deflectors. Effectively, the chopper 104 is acting as a shutter to modulate the light beam in a periodic fashion. The spectrometer 107 may be a grating spectrometer (e.g., a SpectraPro 2150, 600 g/mm grating, Princeton Instrument, NJ) tuned in wavelength and used to select the particular wavelength for testing at a particular instance, where the tuned wavelength is adjusted across an available spectrum or portion thereof. The optical output from the spectrometer is passed through a linear polarizer 112 to make a single polarization of light, thereby avoiding noise affects in the set-up from fluctuating states of polarization. A broadband beam splitter 114 (50:50 ratio) separate the light beam 110 into a reference arm beam 110a and a sample arm beam 110b, each respectively propagating in a reference arm and sample arm of the optical setup 100. Two spatial apertures 117a and 117b are respectively used to match the reference arm beam 110a and sample arm beam 110b diameter sizes. A CCO sample 120 is placed in the sample arm, for example, in a standard 1 ml polystyrene cuvette, while another cuvette 121 filled with only purified water is inserted into the reference arm. In the illustrated example, a matched pair of silicon photodetectors 125a and 125b (e.g., DET100A, Thorlabs, NJ) are used at the output of the sample and reference arms to detect the sample and reference arm beams 110a and 110b. The detectors 125a and 125b output signals to a pair of lock-in amplifiers 130 (SR850, Stanford Research System, CA), which are synchronized to a chopper controller (not illustrated) at 271 Hz (SR540, Stanford Research System, CA). The electronic output from the lock-in amplifier 130 is sent to a computer 135 for data collection and processing (e.g., by LabView 2018, National Instrument). Data from the detected reference arm beam 110a is used to remove errors in the detected sample arm beam 110b. For example, data from the detected reference arm beam may be subtracted, or divided, out of data from the detected sample arm beam to remove fluctuations and errors due to mechanical feature of the optical set-up 100, due to the SCL 102, or from any element in the optical system 100 upstream of the beam splitter 114. The computer 135 may be any processor or device capable of performing the necessary processing to perform the measurements and analysis described herein. For example, the computer 135 may include one or more processors configured to access one or more memories to execute machine readable instructions that cause the processor to perform any of the methods described herein.

In some examples, to enable broadband light generation without excessive pump power levels, a pulsed laser source is used. That is, in some examples, the SCL 102 is a high average power, broadband source that is enabled using picosecond and nanosecond pump pulse regimes with modulational instability initiated SC generation. In addition, this pumping regime yields SC attributes such as a high degree of spectral flatness and relative simplicity in implementation compared to many SC systems that use mode-locked lasers.

Figure 2A:
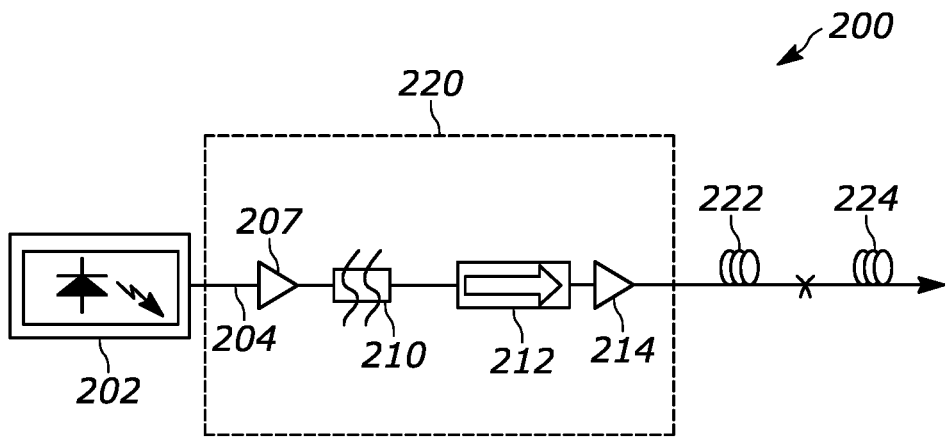
FIG. 2A is a block-diagram of an example super-continuum laser (SCL) which may be implemented in the optical setup of FIG. 1.

In particular, in various examples, the SCL systems herein include an all-fiber-integrated, high-powered light source. FIG. 2A is a block-diagram of an example SCL 200 which may be implemented as the SCL 102 of FIG. 1. The SCL 200 of FIG. 2A includes a light source 202 in the form of a laser diode, which, in this examples, generates an approximately 0.5 ns to ~2 ns pulsed output 204. The pulsed output 204 is amplified in a multiple-stage fiber amplifier 220 designed for optimal noise performance. In the example SCL 200 illustrated in FIG. 2A, the first stage pre-amplifier 207 is an Ytterbium-doped fiber amplifier. For noise optimization, band-pass filters 210 are used between amplifier stages to block amplified spontaneous emission, and isolators 212 are used to prevent spurious reflections. The second stage amplifier 214 is a power amplifier stage such as a cladding-pumped fiber amplifier, e.g., a second Ytterbium-doped fiber amplifier, with performance optimized to minimize nonlinear distortion. In an example, nonlinear distortion is minimized by using a large mode field diameter fiber, so that the intensity is kept lower. Another technique of minimizing distortion is to counter-propagate the pump from the input beam, so that the maximum pump power is toward the distal end of the amplifier gain fiber.

Advantageously, the SCL 200 described herein may be configured into compact form factors by implementing a modulational instability initiated super-continuum source. In examples herein, super continuum light generation occurs in relatively short lengths of fiber that follow the pump laser. In an example, including that of FIG. 2A, a few meters of single-mode fiber 222 (SMF) may be used after the second stage amplifier 214 (i.e., the power amplifier stage), followed by several meters of super-continuum generation fiber 224. In examples, the SMF 222 may be 1 m to 15 m to break up the pulses through modulation instability after the power amplifier. In other embodiments, the SMF fiber 222 may have a length from 0.5 m to 25 m.

In example SCLs herein, the SMF 222 may exhibit peak power of several kilowatts, and the pump light falls in the anomalous group velocity dispersion regime (e.g., the soliton regime). For these high peak powers in this dispersion regime, conventionally, the nanosecond pulses can be unstable due to modulational instability, which is parametric amplification in which the fiber nonlinearity helps to phase-match. As a consequence, the nanosecond pump pulses are broken into many shorter pulses, because modulational instability is trying to form soliton pulses from the quasi-continuous wave background. Although the laser diode (i.e., the light source 202) and amplification starts with nanosecond long pulses, through modulational instability in the short length of SMF 222, about 0.5 psec to several picosecond long pulses are formed with high intensity. Thus, the few meters of SMF 222 results in an output similar to that produced by mode-locked lasers, except the described configuration results in a much simpler and cost-effective implementation.

Accordingly, in example SCL systems, the picosecond or sub-picosecond pulses created through modulational instability in the SMF 222 are coupled into a nonlinear fiber for super-continuum generation (e.g., the super-continuum generation fiber 224). The nonlinear mechanisms leading to broadband super-continuum light include four-wave mixing and/or self-phase modulation, along with the optical Raman effect. Since the Raman effect is self-phase-matched and shifts light to longer wavelength by emission of optical phonons, the super-continuum light spreads to longer wavelengths very efficiently. Therefore, for much of the long wavelength expansion, the Raman effect is the dominant non-linear mechanism. The short wavelength edge arises from four-wave mixing, and often times the short wavelength edge is limited by increasing group velocity dispersion in the fiber. For sufficient peak power and super-continuum fiber length, the super-continuum generation process will fill the long wavelength edge up to the transmission window of the particular fiber used. Thus, with the SCLs described herein, modulation instability initiated super-continuum generation allows for us to design a super-continuum source with no moving parts that helps in reducing motion artifacts and allows for increasing SNR. The resulting light sources are a cascade of fibers pumped by fiber-pigtailed laser diodes and some drive and control electronics. Consequently, the super-continuum sources have the potential to be cost-effective, compact, robust and reliable.

Figure 2B:
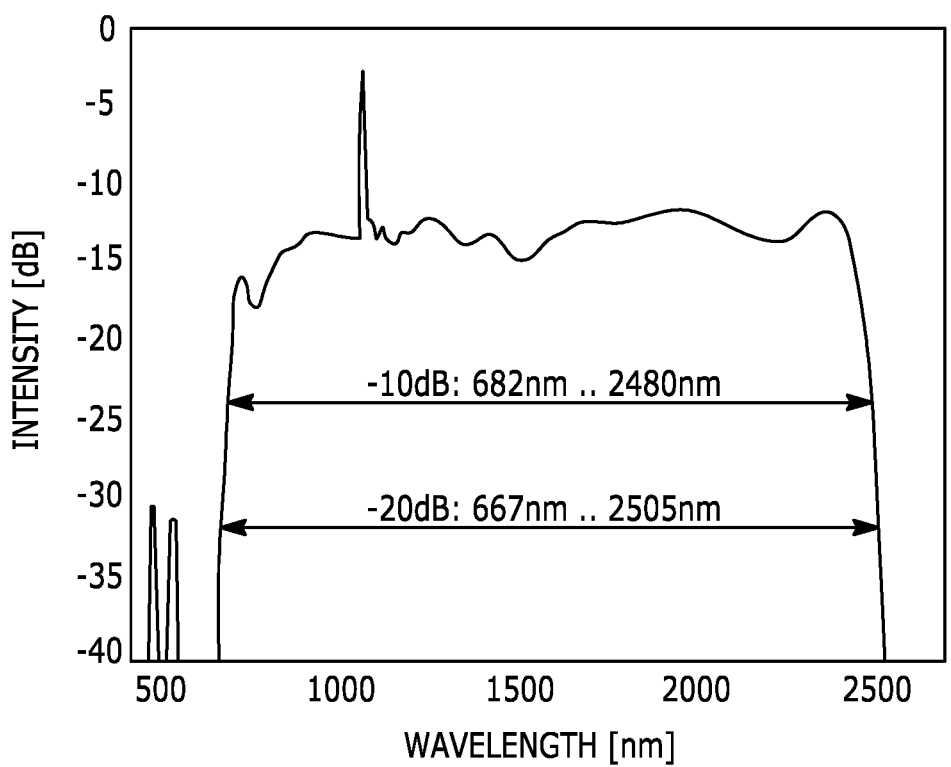
FIG. 2B is a plot of optical output spectrum of an SCL fabricated according to the block diagram of FIG. 2A.

In an example implementation of the SCL 200 of FIG. 2A, the light source 202 was a distributed feedback semiconductor laser that output ~1 ns pulses at an adjustable repetition rate from 100 kHz to 4 MHz. In conjunction with the master-oscillator-power-amplifier design, the SCL 200 provides scalable time-averaged output power between 0.3 W (at 100 kHz repetition rate) to 10 W (at 4 MHz repetition rate) with power stability at +/−0.21% while maintaining roughly the same output spectrum from 670 nm to 2500 nm (FIG. 2B). At the maximum time averaged output power of ~11 W, the wall-plug efficiency for the entire SCL 200 was ~11% (e.g., ratio of output optical power from SCL divided by complete electrical power drawn from the wall for the entire unit—all of the electronics, optics, cooling, etc.). The output beam of the SCL 200 was spatially coherent with a near diffraction limited quality across the entire output spectral range. Since, in the illustrated example, solid core fused-silica fibers were used through-out and transmit over the entire NIR/SWIR range, all of the fibers, fiber-pigtailed components and fiber-pigtailed laser diodes are fusion spliced in the set-up. FIG. 2B is a plot of the optical output spectrum of the SCL 200 fabricated according to the block diagram of FIG. 2A.

Due to the diffraction-limited beam quality, the SCL sources used in SCL systems herein may produce much higher brightness and, therefore, can be coupled into the monochromator or light delivery fibers more efficiently. The enhancement factor depends on the details of a particular experimental configuration. As such, an embodiment of the configuration of FIG. 1 was with the SCL 102 was compare with a system with lamp as the light source to determine an example enhancement factor. As an example, for a fiber bundle of surface area of 1 mm² and a 0.3 numerical aperture, the etendue of the optical fiber is just 0.28 mm². When a black body emitter (emissivity of 0.4) at 3000K temperature was coupled into this fiber bundle, the coupled spectral density was ~0.35 mW/nm at 900 nm. By comparison, at the same wavelength, the SCL 102 source provided a spectral density of ~3 mW/nm, which corresponds to ~8.9 dB higher output power than a conventional light source.

Figure 3:
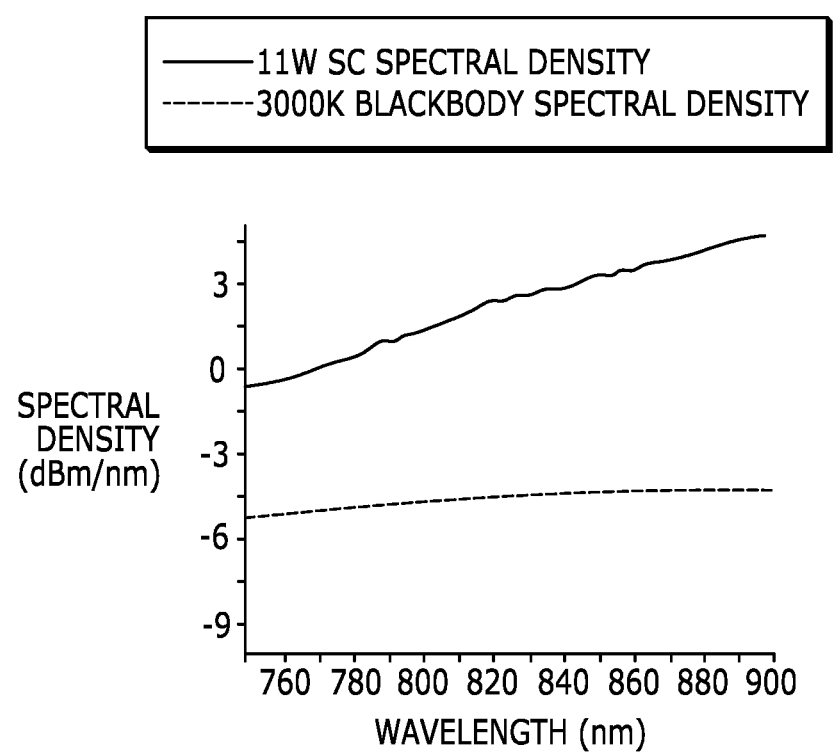
FIG. 3 is a plot of the spectral density versus wavelength for an SCL versus a black body radiator, illustrating a higher spectral density of the SCL.

FIG. 3 is a plot of the spectral density versus wavelength for an SCL (black curve) versus a black body radiator (dotted curve) illustrating the higher spectral density of the SCL. The plotted curve is over the spectral range of 750 nm to 900 nm, the wavelength ranges over which the CCO measurements are conducted, as discussed further herein.

However, at longer wavelengths (e.g., over short wavelength infrared red (SWIR) of approximately 1.4-approximately 3 µm), the spectral density benefit of using the SCL becomes much higher, since the spectral density of the SCL further increases (c.f. FIG. 2B). It should be noted that in the experiments conducted, a monochromator was placed before samples/subjects to extract higher output spectral density while preventing discomfort of a sample or subject, and/or damage to the sample/subject from high power optical illumination.

The SCL systems herein exhibit the sensitivity to measure CCO changes under various metabolic demands, suggesting the ability to detect the same changes occurring in response to injury and illness occurring in a person or an animal. Further discussed herein are a few of the example metabolic conditions and experiments conducted.

Empirical Examples

In an initial example, CCO was assessed in a sample measured in two different metabolic states, oxidized CCO and reduced CCO. In particular bovine heart CCO samples were measured in an oxidized state and in a reduced oxygen state. To prepare the bovine samples, chemicals were added during the experiment to change the oxidation state. The bovine heart CCO (9001-16-5, Sigma-Aldrich) was added as purified enzyme solution in 25 mM Tris-HCl buffer, pH 7.8, 5 mM EDTA, and 39 mM n-dodecyl β--D-maltoside with 5 mg/ml concentration. The molar concentration of the prepared CCO solution was calculated as ~16 µM with estimated molecular weight of 300 kDa.

An SCL system according to the optical setup 100 of FIG. 1 was used to measure the solution, first in the oxidized state and then in the reduced state. Since the resting state of the CCO solution is oxidized state, the optical spectrum of the oxidized CCO was measured first. The reduced state was achieved by adding 80 mM dithionite solution as reductant and waiting 8 mins to achieve fully reduced state. Each state was measured 5 times, and the differential spectrum was obtained by subtracting the averaged spectra of the reduced state from the spectra oxidized state.

Figure 4A:
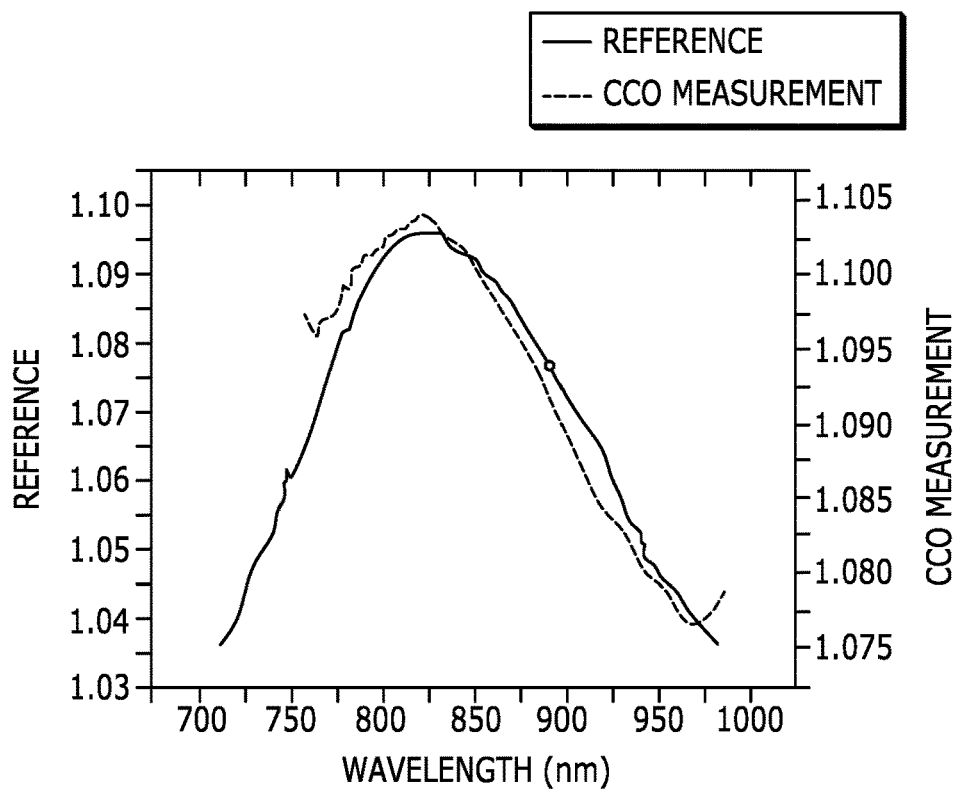
FIG. 4A is a plot of a Cytochrome-C-Oxidase (CCO) optical absorption spectrum.

FIG. 4A is a plot of the CCO optical absorption spectrum measurement described above. The CCO exhibits a broad, featureless spectrum with a peak near 825 nm that stretches primarily between 750 nm and 900 nm. The dotted curve in FIG. 4A is data from the conducted CCO measurement, and the solid curve is CCO reference data reported in the literature. The agreement between the two curves confirms that the conducted experiment was properly measuring CCO.

Figure 4B:
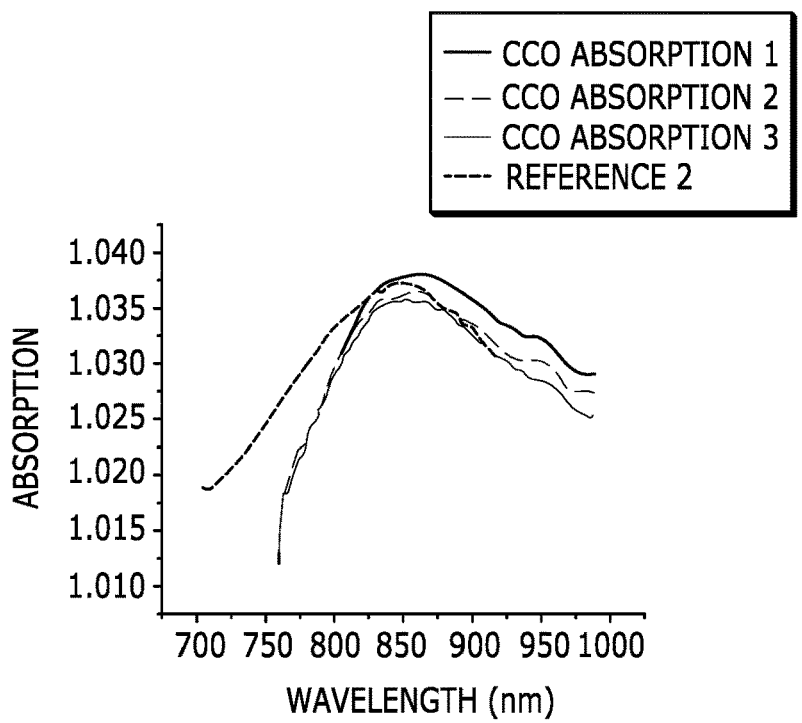
FIG. 4B is a plot of a CCO optical absorption spectrum over time for a given sample

The performed experiments described herein identified that, at least in some examples, the CCO spectrum does shift slightly during experiments, which may be due to different oxidation levels. FIG. 4B is a plot of CCO absorption over time for a given sample. As shown in FIG. 4B, when the CCO spectrum was measured with the cuvette lid closed over a period of minutes, the CCO peak wavelength was seen to shift slightly with the progression over time occurring from CCO absorption 1 to CCO absorption 3. As such, the disclosed SCL systems are able to establish the CCO absorption peak as a function of different cytochrome oxidase groups and states.

As discussed above, in various examples, the SCL systems herein are designed using an all-fiber integrated SCL source to allow for simultaneous measurements of HbO, HbR, and CCO redox state in human subjects.

Figure 5A:
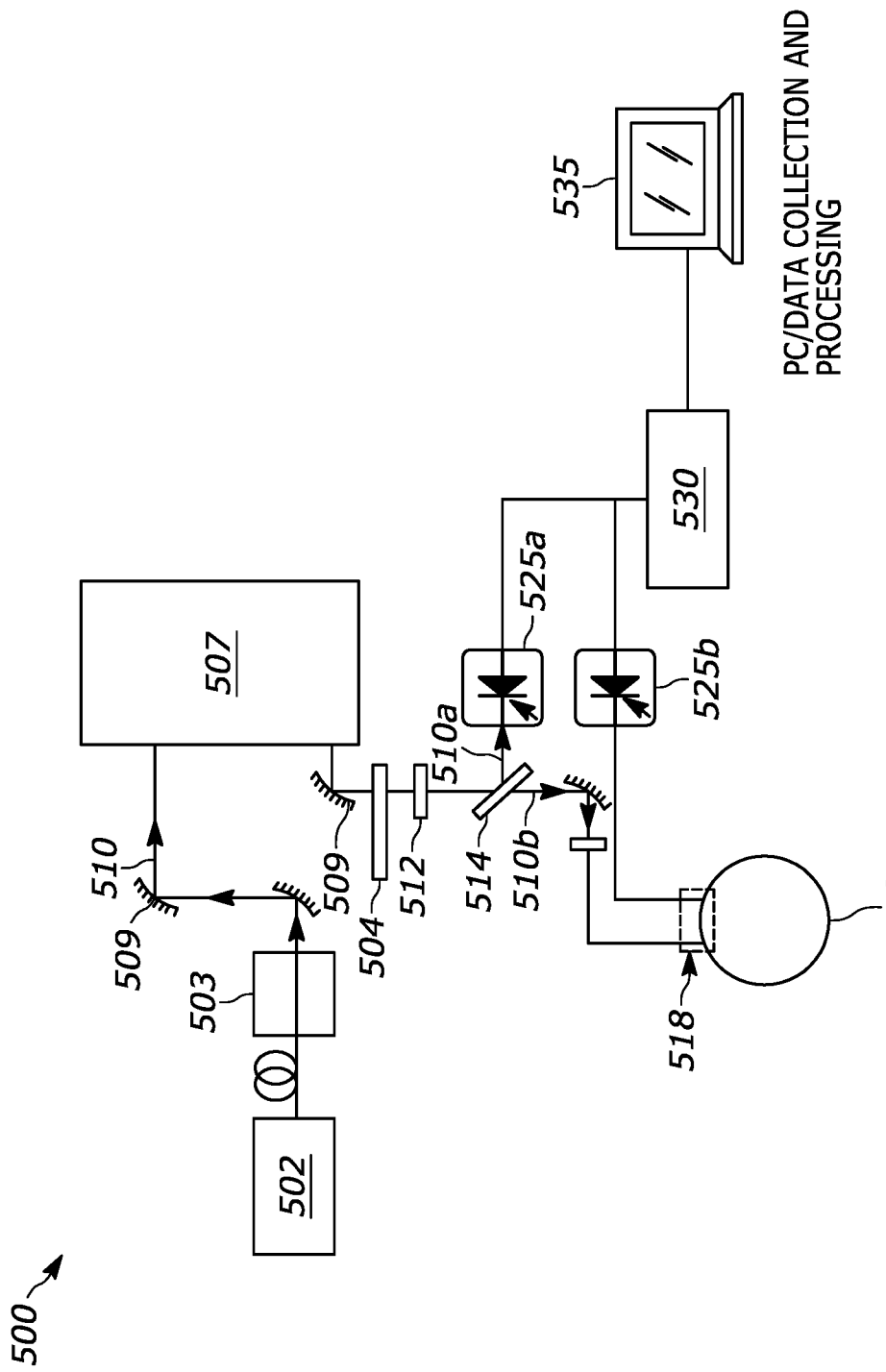
FIG. 5A is a block diagram of an embodiment of an SCL system configuration for detection HbO, HbR, and CCO in a human subject.

FIG. 5A is a block diagram of an embodiment of an SCL system 500 of the configuration of FIG. 1, for detection HbO, HbR, and CCO in a human subject 540. In an example implementation, the SCL system 500 may be implemented as a super-continuum infrared spectroscopy of Cytochrome-C-Oxidase (SCISCCO) system as described herein. The SCL system 500, similar to the system 100 of FIG. 1, uses a NIR/SWIR SCL light source 502 with an output physically coupled to an XYZ stage 503 followed by a tunable spectrometer 507, optical chopper 504, and polarizer 512. Mirrors 509 are used to guide the beam throughout parts of the SCL system 500. The light source 502 outputs a beam 510, mirrors 509 guide the beam 510, and a beam splitter 514 (99:1 ratio) is used to split the beam 510 into a reference arm beam 510a and sample arm beam 510b, that respectively propagate in reference and sample arms of the SCL system 500. The reference arm beam 510a is sent to a first silicon detector 525a, and this is used to divide out the laser fluctuations from the sample arm beam 510b during data processing. The sample arm beam 510b is coupled into a fiber-based probe 518 for delivery of light to, and collection of light from, the human subject 540. The collected light from the human subject 540 is then provided to a second silicon detector 525b. The output from the first and second silicon detectors 525a and 525b in the reference and sample arms are sent to a lock-in amplifier 530 synchronized to the optical chopper 504. The output from the lock-in amplifier 530 is sent to a computer 535 for data collection and analysis. The computer 535 may include one or more processors configured to execute machine readable instructions that cause the computer 535, and any processors thereof, to perform the methods described herein, such as the methods described in reference to FIGS. 6A, 6B, methods or processes of the tests described in reference to FIG. 7A through FIG. 20, or another method for performing any of the measurements or analyses described.

FIGS. 5B and 5C illustrate exemplary probe ends 560 of the fiber-based probe 518 of the SCL system 500 of FIG. 5A. A sensor housing 567 may be fixedly connect to a super-continuum fiber probe, for placement on the human subject 540 for blood pressure tests and breath holding tests as described herein. As described further below, a modified probe end may be used in the attention test. In the illustrated examples of FIGS. 5B and 5C, an output fiber 562 is used for SCL light delivery through an output 563 of the output fiber 562, and an input fiber 564 captures reflected light through an input 565 of the input fiber 564. Each of the output and input fibers 562 and 564 included a 2 mm diameter borosilicate fiber bundle with SMA connectors on both ends of each of the fibers 562 and 564. The two fibers 562 and 564 were mounted on a solid base of the sensor housing 567. Although the distance between the output 563 and the input 565 is adjustable, the experiments described herein were conducted with a spacing of 2 cm between the output 563 and input 565 of the respective output and input fibers 562 and 564. For a "banana pattern" optical penetration pattern, this would mean that signals are measured from a ~2 cm penetration into the sample or skin. In this way, the probe 518 is configured for use on the forearm for the blood pressure tests and on the forehead for the breath holding test. The scan depth of the probe 518 may be determined by the spacing distance between the output 563 that provides light to the subject 540 and the input 565 that collect light reflected from the subject 540. For example, a 2 cm spacing distance between the output 563 and the input 565 would lead to an approximate 2 cm penetration depth, i.e., measured in the z-axis. Thus, in some examples, the probes (i.e., the output and input fibers 562 and 564) described herein may be configured to provide adjustable spacing distances between probe ends (i.e., the output 563 and the input 565), for example through an adjustment MEMs structure, such as a rail structure or other slidable engagement. As described herein, the output and input fibers 562 and 564 may be referred to as a source fiber and collector fiber respectively due to the fact that the output fiber 562 provides the SCL light acting as a light source for the probe 518, and the input fiber 564 collects the reflected SCL light.

Figure 6A:
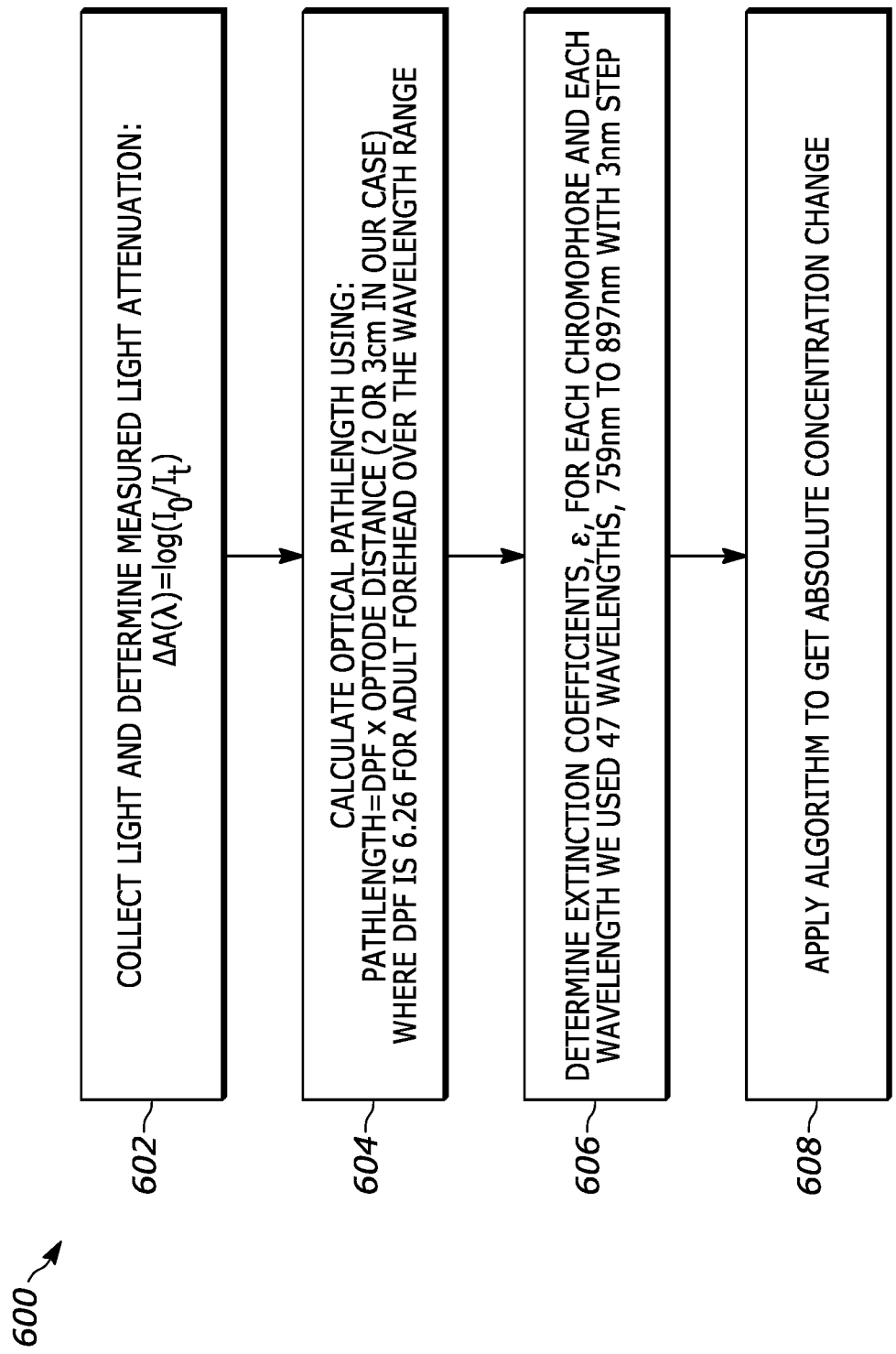
FIG. 6A is a flow diagram of a method to measure the absolute concentration change in CCO.

FIG. 6A is a flow diagram of a method 600 to measure the absolute concentration change in CCO. The measured wavelength dependent optical intensity change was converted into CCO using a modified Beer-Lambert law-based algorithm executed by a computer processing system, such as the computer processing system 535 of FIG. 5A. The algorithm attributes the intensity changes across the wavelength range to the absorption changes of 3 chromophores: HbO, HbR, and CCO. Referring simultaneously to FIGS. 5A and 6, at a block 602, reflected light is collected from a sample (e.g., the subject 540) by the SCL system 500, light attenuation as a function of wavelength is determined. Next, at a block 604, the optical pathlength of the collected light was calculated as a function of differential pathlength factor (DPF) and optode distance. The DPF changes with different areas on the sample or subject 540 under examination. At a block 606, the extinction coefficients, ε, for each chromophore were determined, and at a block 608, the absolute concentration changes of the HbO, HbR, and CCO were calculated. In the illustrated example, the algorithm used a least-square fitting to back-calculate the concentrations. To get the absolutely concentration change in each of the chromophores, HbO, HbR, and CCO, the algorithm was configured to use the extinction coefficient ε for each chromophore, differential pathlength factor (DPF), delivery-pickup fiber distance d (i.e., the distance between the output 563 and the input 565), and intensity change at each wavelength $I_0(\lambda)/I_t(\lambda)$:

$$\begin{bmatrix} \Delta[HbO] \\ \Delta[HbR] \\ \Delta[CCO] \end{bmatrix} = \frac{1}{DPF \times d} \times \begin{bmatrix} \varepsilon_{HbO}(\lambda_1) & \varepsilon_{HbR}(\lambda_1) & \varepsilon_{CCO}(\lambda_1) \\ \varepsilon_{HbO}(\lambda_2) & \varepsilon_{HbR}(\lambda_2) & \varepsilon_{CCO}(\lambda_2) \\ \vdots & \vdots & \vdots \\ \varepsilon_{HbO}(\lambda_n) & \varepsilon_{HbR}(\lambda_n) & \varepsilon_{CCO}(\lambda_n) \end{bmatrix}^{-1} \begin{bmatrix} \log(I_0(\lambda_1)/I_t(\lambda_1)) \\ \log(I_0(\lambda_2)/I_t(\lambda_2)) \\ \vdots \\ \log(I_0(\lambda_n)/I_t(\lambda_n)) \end{bmatrix}.$$

In example experiments described herein, 47 wavelengths from 759 nm to 897 nm were used. The parameters for the above formula were selected as follows: specific extinction coefficient was that provided in Kolyva et al. (Kolyva, C., Tachtsidis, I., Ghosh, A., Moroz, T., Cooper, C. E., Smith, M., & Elwell, C. E., "Systematic investigation of changes in oxidized cerebral cytochrome c oxidase concentration during frontal lobe activation in healthy adults," Biomedical optics express, 3(10), 2550-2566 (2012)), DPF was estimated to be 6.26 for an adult's forehead, and the delivery-pickup fiber distance d was 3 cm for the attention test and the breath holding test, while it was 2 cm for the blood pressure test.

Figure 6B:
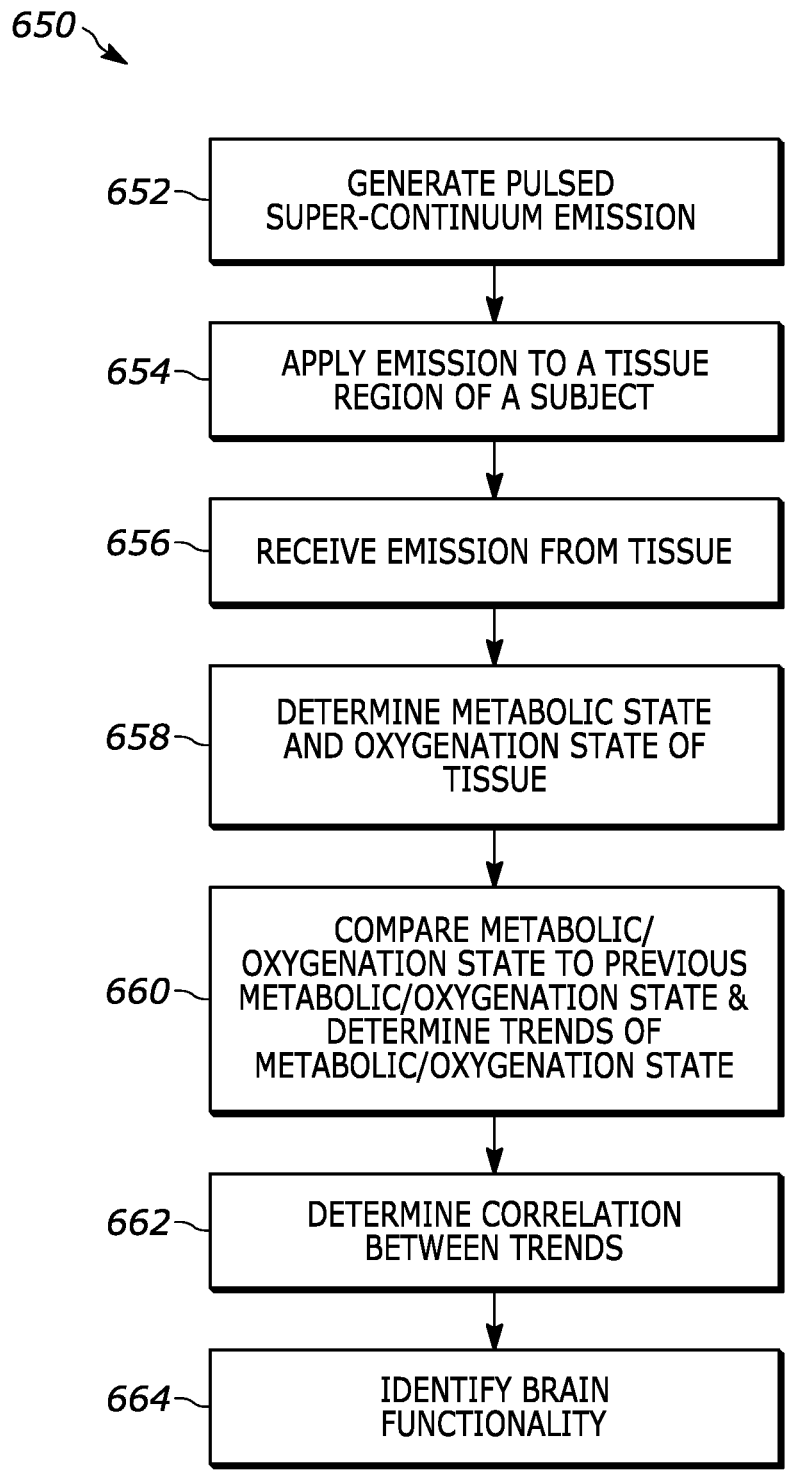
FIG. 6B is a flow diagram of a method 650 for measuring the metabolic state of a brain tissue.

FIG. 6B is a flow diagram of a method 650 for measuring the metabolic state of a subject. The method 650 was used to perform at least some of the parts of the following example measurements. Further, the method 650 may be performed by the SCL system 500 of FIG. 5, or by another system capable of providing super-continuum light. Referring simultaneously to FIGS. 5A and 6B, at a block 652, the SCL light source 502 generates a super-continuum emission. The super-continuum emission being light that has a wavelength in at least one of the near infrared (NIR) or the short-wave infrared (SWIR) wavelength range. Further, the emission may be a continuously radiative emission, or a pulsed radiation emission. The SCL light source 502 may include multiple amplification stages formed of one or more of a fiber pre-amplifier stage, an optical noise filtering stage, a fiber amplifier stage, or another amplification or filtering stage. The SCL light source 502 may be configured as the example SCL 200 of FIG. 2A.

At a block 654, the method 650 includes applying the super-continuum emission to a region of tissue of a person or an animal. In a person, the emission may be applied to a forehead, temple, scalp, forearm, leg, chest, or another body part of the subject. Further, measurement can be applied to animals or other biological samples having metabolic function. The super-continuum emission may be applied to the tissue by using a probe. In examples, the probe may be the probe 518 of FIGS. 5A, 5B, and 5C. The probe 518 may include a probe housing 567 that is physically coupled to two optical fibers. First, the probe 518 includes a source fiber (i.e., the output fiber 562) configured to receive the super-continuum emission, either directly or indirectly, from the SCL light source 502. The source fiber has an output, such as the output 563 of FIGS. 5B and 5C, physically position to provide the super-continuum emission to the tissue. Further, the probe housing 567 of the probe 518 is fixedly connected to a collection fiber (i.e., the input fiber 564) configured to receive light from the tissue of the person or an animal. The collection fiber has an input, such as the input 565 physically position to collect scattered, and reflected light from the tissue (i.e., reflected super-continuum emission). At a block 656, the collection fiber receives the emission from the tissue and the collection fiber is configured to provide the received emission to a detector, such as the second silicon detector 525b of FIG. 5A.

Then, at a block 658, a metabolic state and oxygenation state of the tissue is determined. The metabolic and oxygenation states may be determined from one or more of a metabolic chromophore and one or more oxygenation chromophores. In examples, the computer 535 performs processes, such as the method 600 of FIG. 6A, to determine one or more of the metabolic state and/or the oxygenation state of the tissue. The metabolic chromophore may include CCO, and the oxygenation chromophore may include oxygenated hemoglobin and/or deoxygenated hemoglobin.

At a block 660, the measured metabolic state is compared to a previous metabolic state to determine a trend of the metabolic state, and the measured oxygenation state is compared to a previous oxygenation state to determine a trend of the oxygenation state. To compare the measured metabolic and oxygenation states to previous states, the method 650 may include determining a redox CCO spectral profile, a HbO spectral profile, and/or a HbR spectral profile. The method 600 then determines, at a block 662, a correlation between the determined trends of the metabolic and oxygenation states. The correlation may be a positive linear correlation, a negative linear correlation (i.e., a linear discorrelation), a Pearson correlation, a Kendall correlation, a Spearman correlation, a nonlinear correlation, or a non-correlation (i.e., no correlation). At a block 664, brain metabolism is identified from the correlation, which may be used to assist in determining a brain functionality. For example, a negative correlation between CCO and HbO may indicate normal brain metabolism and normal brain functionality while a human subject is focusing on a task, while a non-correlation between CCO and HbO may indicated abnormal brain metabolism and therefore may be indicative of abnormal brain functionality. The correlation may further be useful in identifying a number of specific diagnosis of the abnormal brain metabolism. For example, the correlation may assist in diagnosis of a concussion, tumor, hemorrhage, ischemia, shock, stroke, or infarction. Beyond diagnosis of specific conditions, there is the potential to prognosticate outcomes based, which would be particularly valuable for more severe conditions where it is difficult to gather empiric data. For more mild conditions, such as concussion, normalization of brain metabolism could help guide decisions on returning to normal activity levels. Further, the systems and methods may be useful for monitoring metabolic function and organ functionality during surgery, during a medically induced coma, during sedation, and for neonates. Accordingly, the technologies described may be useful in prehospital settings, emergency rooms, inpatient and outpatient environments, and the operating room.

The correlation may be identified by comparing a redox CCO spectral profile, a HbO spectral profile, and/or a HbR spectral profile. The correlation may include trends between a set of metabolic states over time, compared to a set of oxygenation states over time for example, a correlation may be determined that during a time, the metabolic state increases while the oxygenation state decreases, or the metabolic and oxygenation state increase, or decrease, together. Other correlation types between the data are envisioned, such as identifying dis-correlations and non-correlations, as previously described.

The method 600 may be implemented over long periods of time, continuously or intermittently. For example, multiple measurements as performed by the method 600 may be performed on a human subject or animal subject continuously during an operation that requires monitoring of brain metabolism and/or brain functionality. Another implementation of method 600 may include periodic checkups at a clinic where the method 600 is performed one every few days, or weeks to monitor brain metabolism and/or brain functionality during a long term treatment such as the use of medication, or during recovery from a surgery or traumatic event.

Measurements and tests performed by the methods 600 and 650 may be performed to a specific measurement protocol, for example, the measurements may be performed according to a blood pressure test protocol, breath holding testing protocol, a concussion testing protocol, an attention testing protocol, or another protocol. Further, multiple protocols may be implemented simultaneously to perform multiple tests on a single human or animal subject (also termed herein "participant"). Additionally, the term "test protocol" may be used interchangeable herein with the term "measurement protocol". In various examples, tests and measurements described herein were performed on human participants. In embodiments, the systems and methods disclosed may be used to measure metabolic and organ functionality of any subject. The term "subject" as used herein includes a living mammal, including, but not limited to, mammals of the order Rodentia, such as mice and hamsters, mammals of the order Logomorpha, such as rabbits, mammals from the order Carnivora, including Felines (cats) and Canines (dogs), mammals from the order Artiodactyla, including Bovines (cows) and Swines (pigs), and mammals of the order Perssodactyla, including Equines (horses). In some aspects, the mammals are of the order Primates, Ceboids, or Simoids (monkeys), or of the order Anthropoids (humans and apes). In various aspects, such as the examples described herein, the subject is a human.

Figure 7A:
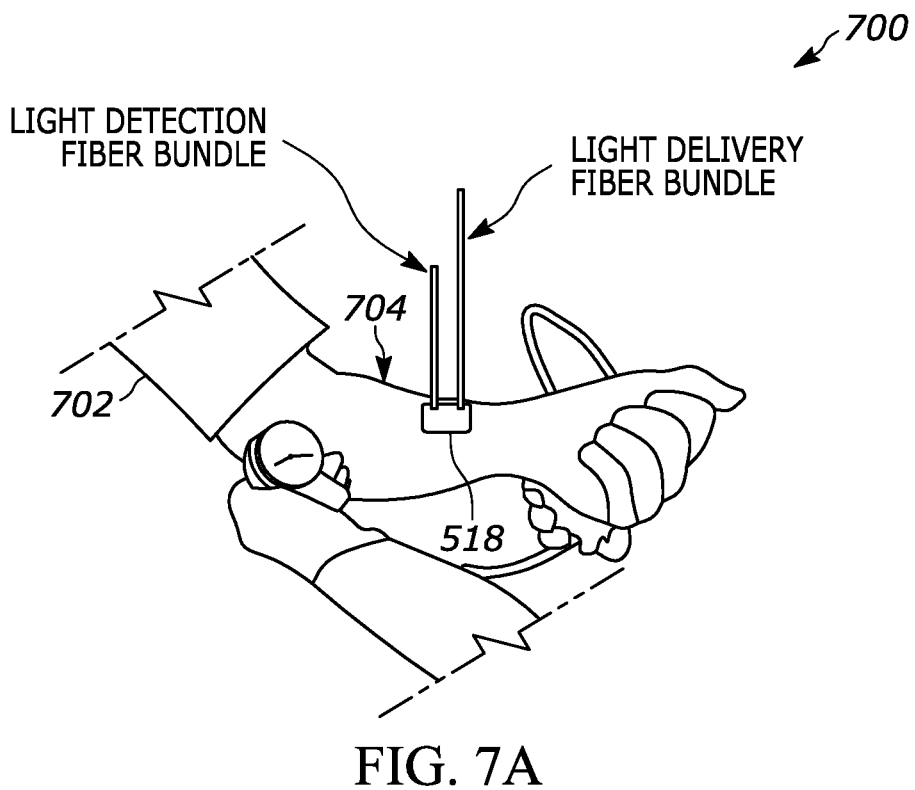
FIG. 7A illustrates an example test set-up for a blood pressure test
Figure 7B:
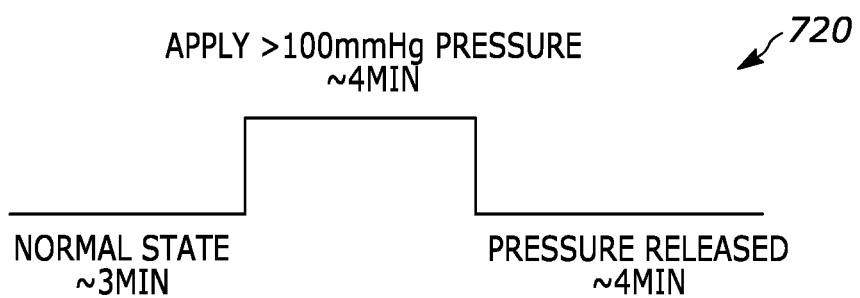
FIG. 7B illustrates an example measurement protocol for the blood pressure test of FIG. 7A.

Blood Pressure Test at Forearm Example: In an example experiment, an embodiment of a SCL system was tested and validated against reference data reported that used a commercial super-continuum source in the form of a mode-locked laser for a blood pressure test. FIG. 7A illustrates the set-up 700 for the blood pressure test, and FIG. 7B illustrates a protocol 720 for the blood pressure test. A blood pressure cuff 702 was wrapped on an upper arm 704 of a human subject for inducing blood pressure changes to the individual. Additionally, the probe 518 of FIGS. 5B and 5C configured within the SCL system 500 of FIG. 5A, was applied to the forearm 704 on the same side of the forearm 704, after which the SCL system 500 measured HbO, HbR, and CCO. The test protocol 720, as shown in FIG. 7B, was maintained with a healthy human subject in a normal state (i.e., not inflated cuff) for about three minutes, then the cuff was inflated to above 100 mmHg pressure for four minutes, after which the pressure is released for about four minutes. The spectrum of the diffusely reflected light was measured continuously through the test, with each complete spectrum measurement requiring about 30 seconds due to the speed of the mechanical rotation of a grating in the spectrometer 507 of FIG. 5A (note: in the attention test discussed further herein, the data collection was optimized to reduce the scan time to ~17 sec).

Figure 8:
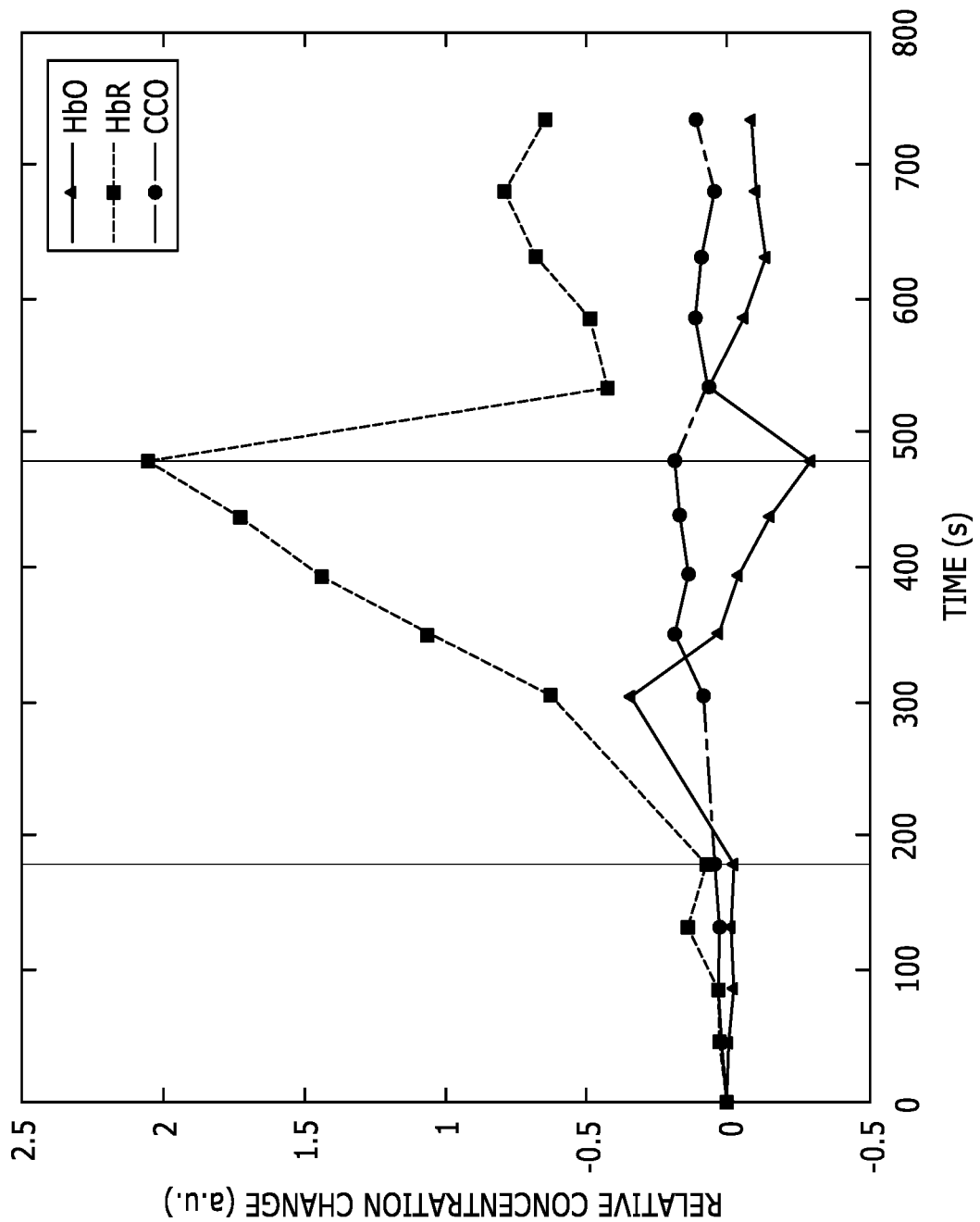
FIG. 8 illustrates measured changes in oxygenated hemoglobin (HbO), deoxygenated hemoglobin (HbR), and the redox state of CCO during a blood pressure test.

FIG. 8 illustrates the measured HbO, HbR, and CCO and correlations and dis-correlations that resulted, in an example blood pressure test. As shown in the plot of FIG. 8, after applying the cuff pressure the HbR increases, the HbO decreases, and the CCO remains relatively unchanged (i.e., within the noise of the measurement). The results of FIG. 8 are similar to that obtained in (Lange, F., Dunne, L., Hale, L., & Tachtsidis, I., "MAESTROS: a multiwavelength time-domain NIRS system to monitor changes in oxygenation and oxidation state of Cytochrome-C-Oxidase," IEEE Journal of Selected Topics in Quantum Electronics, 25(1), 1-12 (2018)), thereby validating that the example SCL system 500 matched previously reported literature measurements of CCO using different kinds of super-continuum light sources.

The reason the CCO does not change in the forearm may be because of several reasons. First, the forearm muscles have a relatively low level of CCO, compared, for example, to the brain. Second, for only a 4-minute tightening of the pressure, there is blood constriction, but there is not expected to be a significant change in muscle metabolism since muscle is less affected by oxygen deprivation.

Breath Holding Test at Forehead Example: An example SCL system was further used to assess HbO, HbR, and CCO correlations during a breath holding test. The SCL system results were compared with a commercial fNIRS system (CW6, TechEn Inc.). The fNIRS only provided information regarding HbO and HbR, although typically the results for HbR are noisier and less reliable using other conventional systems. The SCL system, by contrast, was used to derive HbO, HbR and CCO, allowing the comparison between the results for HbO and HbR against CCO. If the HbO and HbR measurements are relatively consistent, then the CCO measurement can be reasonably asserted to be reliable.

Figure 9A:
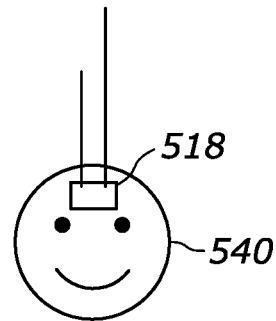
FIG. 9A illustrates an example test set-up for a breath holding test.
Figure 9B:
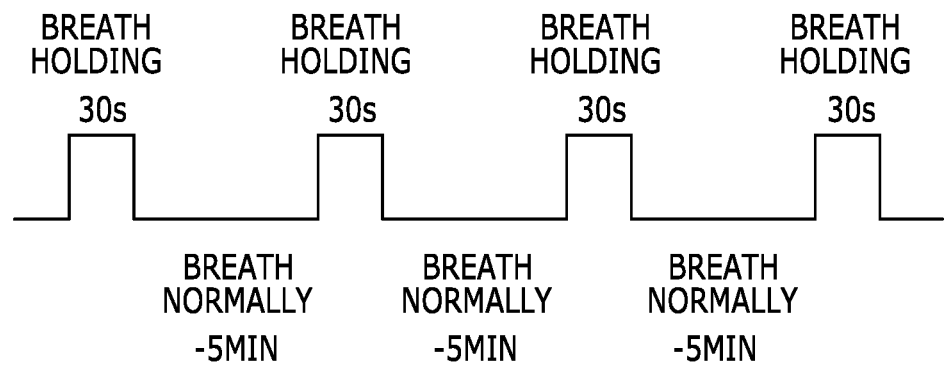
FIG. 9B illustrates an example measurement protocol for the breath holding test of FIG. 9A.

FIGS. 9A and 9B respectively illustrate an example test set-up and protocol for the breath holding test. The probe 518 of FIGS. 5B and 5C, configured within the SCL system 500 of FIG. 5A, was applied to the forehead of a healthy human subject 540. For the fNIRS system comparison test, the fNIRS probes were placed on the left and right sides of the head of the subject 540. All of the fNIRS probes were secured with a silicone rubber band, and the input 565 and output 563 separation of the probe 518 for the SCL system 500 was 3 cm.

As illustrated in FIG. 9B, the protocol was for the human subject to breath normally for about 5 minutes, hold the breath for 30 seconds, and then the sequence is repeated multiple times. The spectrum was measured continuously, with each spectral scan requiring about 30 sec to collect due to the speed of tuning of the spectrometer.

Figure 10:
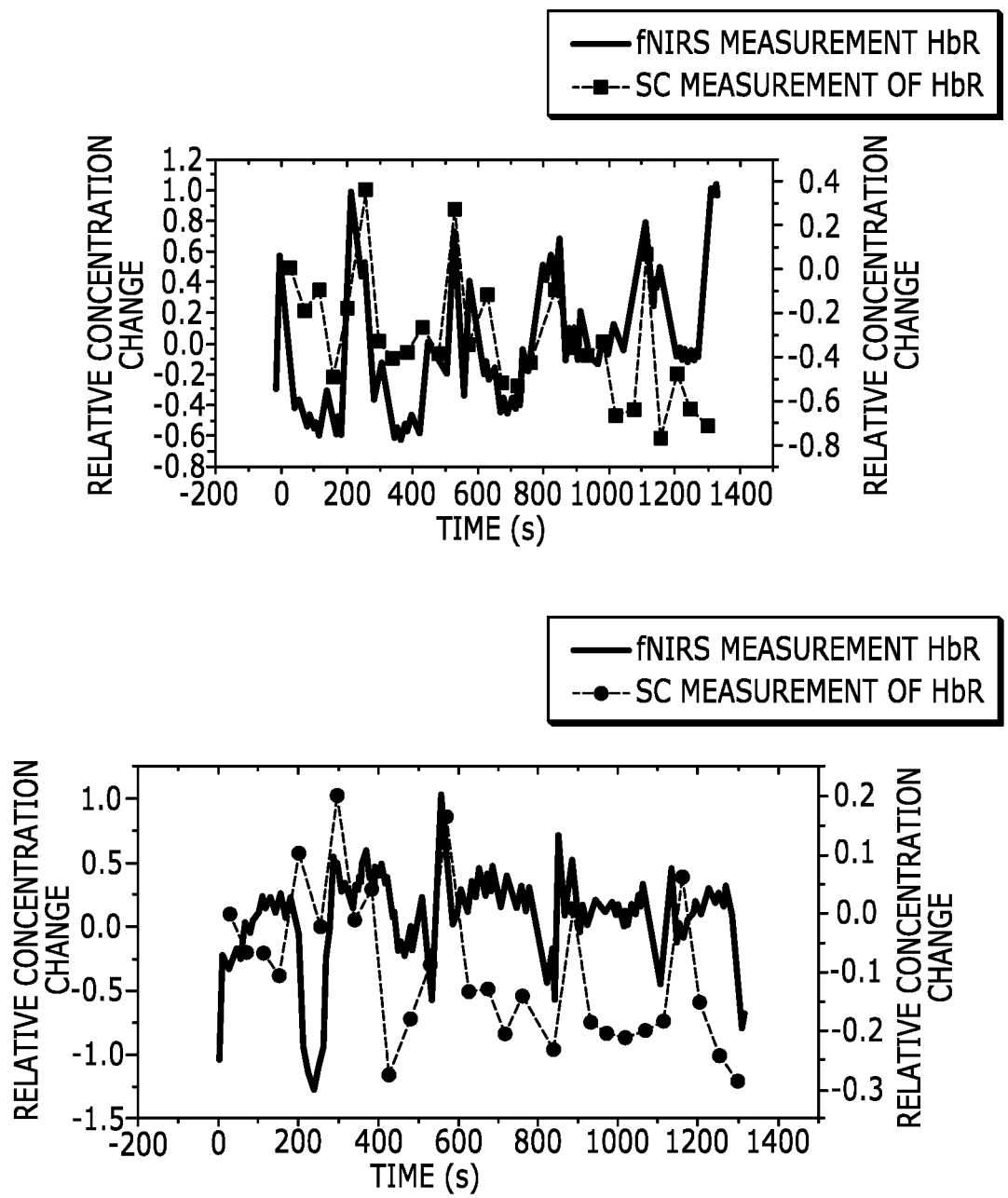
FIG. 10 illustrates plots showing the comparison between simultaneous measurements of a fNIRS system and an SCL system for the breath holding test of FIGS. 9A and 9B.

FIG. 10 illustrates plots showing the comparison between the fNIRS system, as the solid curve on the plots, and the SCL system, as the dotted curve, for simultaneous measurements during the breath holding test. The top plot shows the comparison for HbO, with the shaded regions corresponding to the breath holding periods. Both systems show that the HbO increases during the breath holding period, and there is reasonable correlation between the two measurements types. The bottom plot shows the comparison for HbR for the two different measurement types, where the results are generally similar, but the correlation is not as good. It should be noted that in fNIRS systems the HbR tends to be noisier, in part because the sensitivity at the shorter wavelengths is less for that type system. Similar rationale may also apply to the SCL system. Moreover, the discrepancy between the two systems may also be in part attributable to changes in HbO concentration during the breath holding periods and the low sampling rates of the SCL system that failed to capture this dynamic consistently. During breath holding, HbO increases during the first 10-20 seconds, followed by a decline in HbO concentration. Yet, the example SCL system used we measured about every 30 seconds, we may have mis-captured this dynamic in terms of its rise and fall during the breath holding period.

Figure 11A:
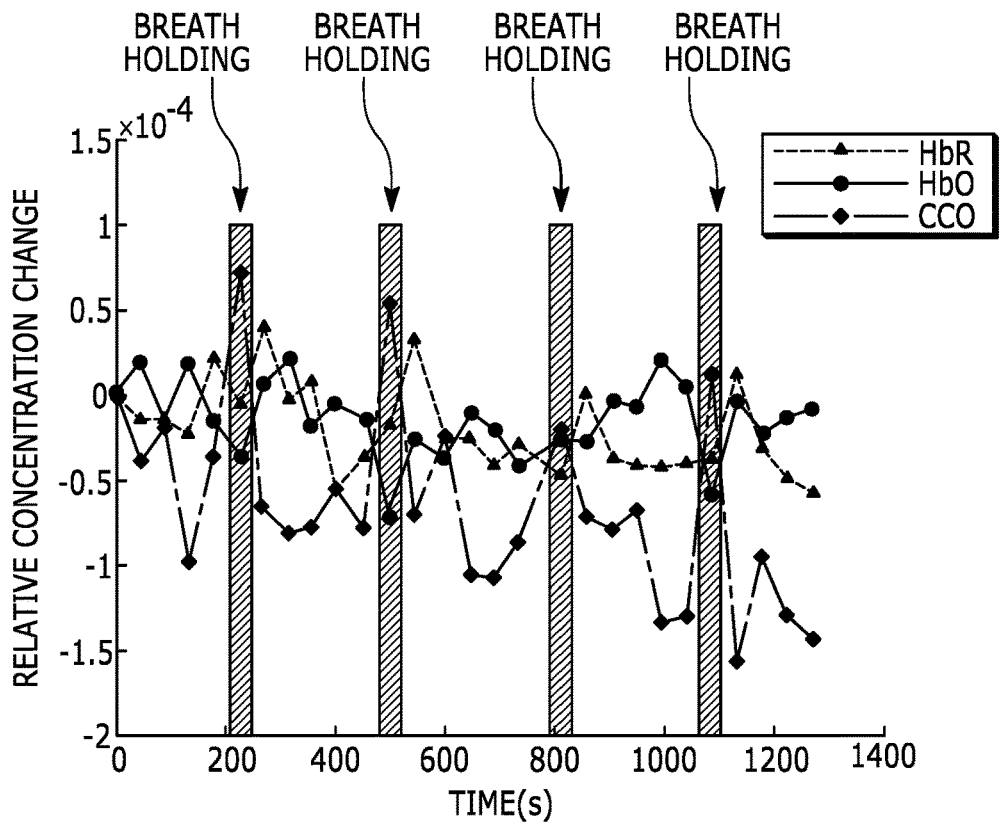
FIG. 11A illustrates the correlations between CCO and HbO and HbR resulting from the SCL system breath holding test of FIGS. 9A and 9B.
Figure 11B:
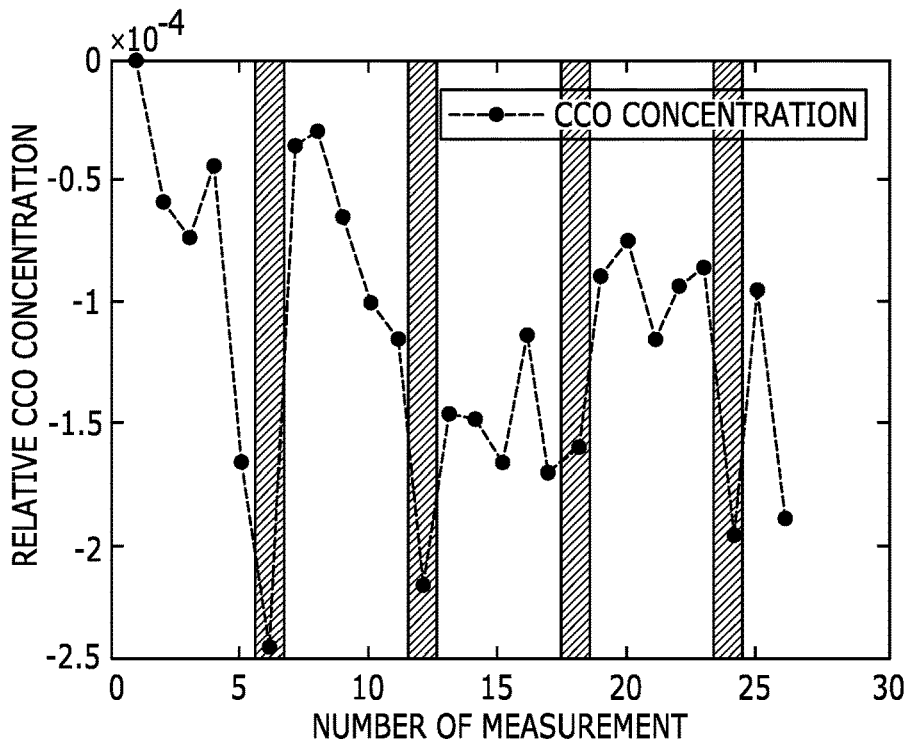
FIG. 11B illustrates the CCO measurements for the breath holding test in greater detail than FIG. 11A.

FIGS. 11A and 11B illustrate results from the SCL system breath holding test, showing the correlations between CCO and HbO and HbR. FIG. 11A shows the overlap of the HbO, HbR, and CCO signals through the protocol, with the shaded regions corresponding to the periods of breath holding. FIG. 11B illustrates the CCO measurements for the breath holding test in greater detail. The curves of FIGS. 11A and 11B result from averaging five measurements from three different healthy human participants or subjects, with each subject being measured three times. FIGS. 11A and 11B show that for at least three out of the four breath holding periods, the CCO level decreased during the breath holding period.

The breath holding test confirmed that the SCL system's signal reflects the same hemodynamic response detected by the fNIRS measurements. As previously discussed, the measurements of HbO obtained with the two systems correlate more closely than the measurements of HbR. This result is expected due to higher noise levels affecting HbR more than HbO. The observed hemodynamic response induced by the breath holding test is consistent with expectations based on published literature. For example, Emir, U. E., Ozturk, C., & Akin, A., "Multimodal investigation of fMRI and fNIRS derived breath hold BOLD signals with an expanded balloon model," Physiological measurement, 29(1), 49 (2007) finds that HbO increases during the breath holding period and HbR increases after the end of the breath holding period. This pattern is again reflected in the results presented in FIG. 10. The breath holding test is a physiological test that mimics the effects of oxygen deprivation to observe the protective response of brain cells when energy supplies run low. The SCL system was also tested in a cognitive test, described below, which mimics the effects of increased brain metabolism or an increased need for oxygen that outpaces the supply. The SCL system and the fNIRS device produced similar results in response to these tests, which confirmed the expected hemodynamic responses in each case.

Attention Test Example: An example SCL system was further used to assess HbO, HbR, and CCO correlations under cognitive loading during a test of attention. In the experiment 25 healthy human subject were asked to perform complex tasks that required intense involvement of the frontal portion of the brain located in the region of the forehead. The subject each needed to focus on the target information, ignore distractors, and remember the rules or instructions to complete the task. The frontal lobe is responsible for performing these aspects of attention. Measurements of the frontal lobe brain metabolism obtain by the SCL system were compared against those obtained with a commercial fNIRS system.

Figure 12A:
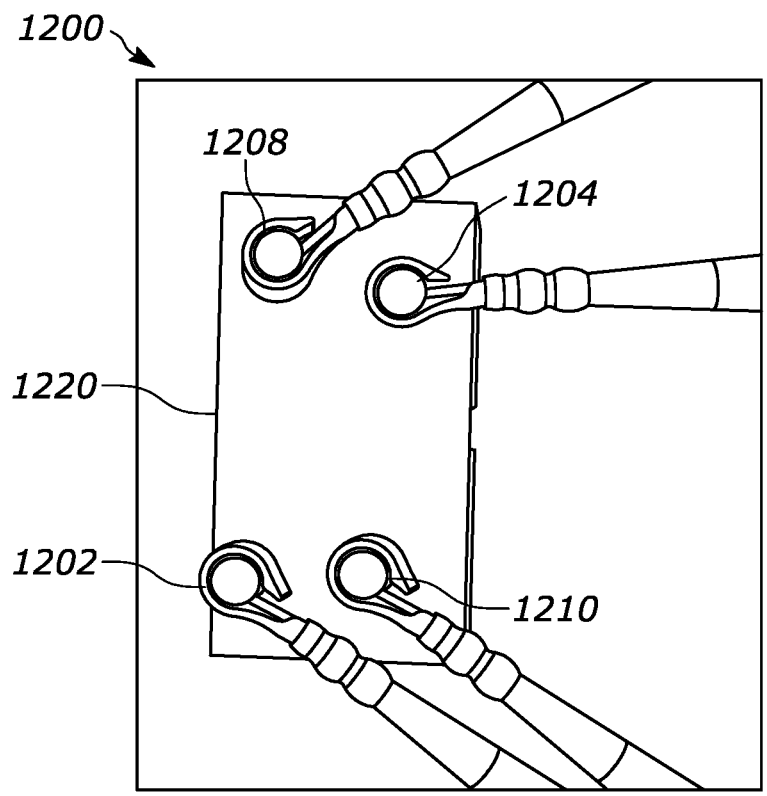
FIG. 12A illustrates a front perspective view of a modified CCO probe that integrates probes for both an SCL and fNIRS system.
Figure 12B:
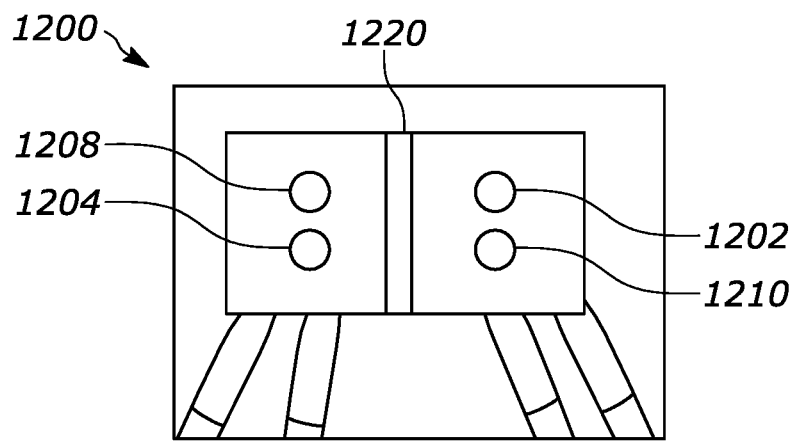
FIGS. 12B and 12C illustrates a back perspective view of a modified CCO probe that integrates probes for both an SCL and fNIRS system.
Figure 12C:
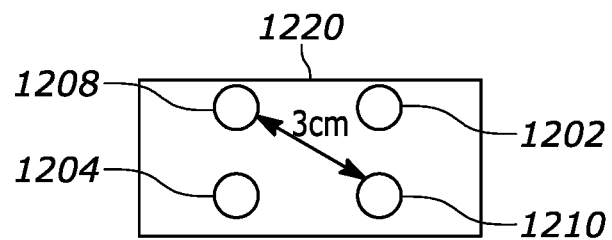

Correlations between conventional fNIRS systems and the example SCL system may be affected by the location of the probes. A modified probe was developed to eliminate this variable. The probe used during the attention test included both an fNIRS fiber and an SCL system collection fiber to obtain data from the same region of the forehead. FIGS. 12A and 12B (and 12C) respectively illustrate a front and a back view of a modified CCO probe 1200 that integrated the various inputs and outputs of the SCL and fNIRS systems. The new probe 1200 includes an SCL output 1202, and an SCL input 1204 disposed on opposite corners along a diagonal of a rectangular probe housing 1220. The probe 1200 further includes an fNIRS input 1208 and fNIRS output 1210 disposed on opposite corners of the second diagonal of the rectangular probe housing 1220. Each of the SCL and fNIRS inputs 1204 and 1208 is coupled to an optical fiber, and each of the SCL and fNIRS outputs 1202, and 1210 is also coupled to an optical fiber. The output fibers and the input fibers for each of the SCL and fNIRS systems were place approximately three centimeters apart along the corresponding diagonals.

Figure 13A:
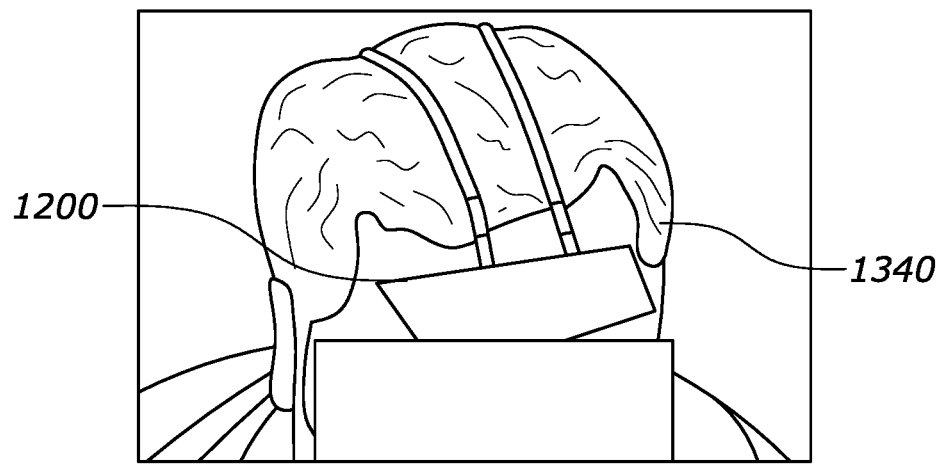
FIG. 13A illustrates an example test set-up for an attention test using the modified probe of FIGS. 12A-12C and 12B.
Figure 13B:
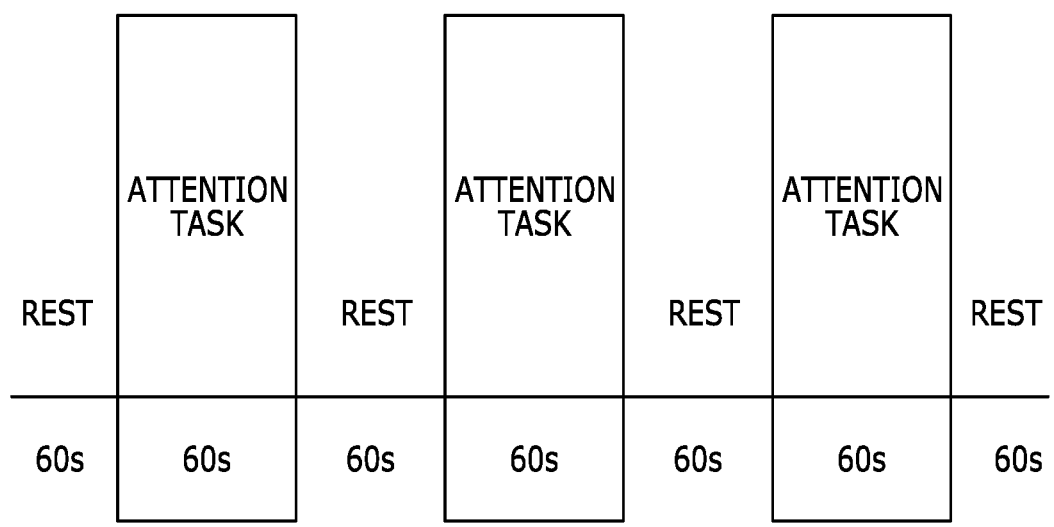
FIG. 13B illustrates an attention measurement protocol for the attention test set-up of FIG. 13A.

FIGS. 13A and 13B illustrate the modified CCO probe 1200 location on a human subject 1340 and the attention test protocol, respectively. The CCO probe 1200 was placed with 3 cm separation on the forehead. The fNIRS probe includes a regular band at the left and right hemisphere, and one reference channel at the forehead. The probe 1200 is taped to the forehead of the subject to minimize motion artifacts during the measurement.

FIG. 13B shows that the attention test protocol included three task blocks, and then the test was repeated three times (i.e., for each participant there are nine blocks in total of the attention task). Each cycle of the protocol included a 60 second rest period followed by a 60 second attention test, which was repeated three times in the same test, and ended with a 60 second rest period. This protocol was repeated three times for a given participant. The description of the cognitive attention test was as follows. The participant would see a capital letter (e.g., A- B- C- D-) followed by a lowercase letter (e.g., a- b- c- d-) and sometimes the two letters were the same, sometimes they were different. The participant was asked to press a key corresponding to the small letter, when the small letter was observed (e.g., when the letter "b" was shown, the participant pressed the letter b on a keyboard).

Figure 14:
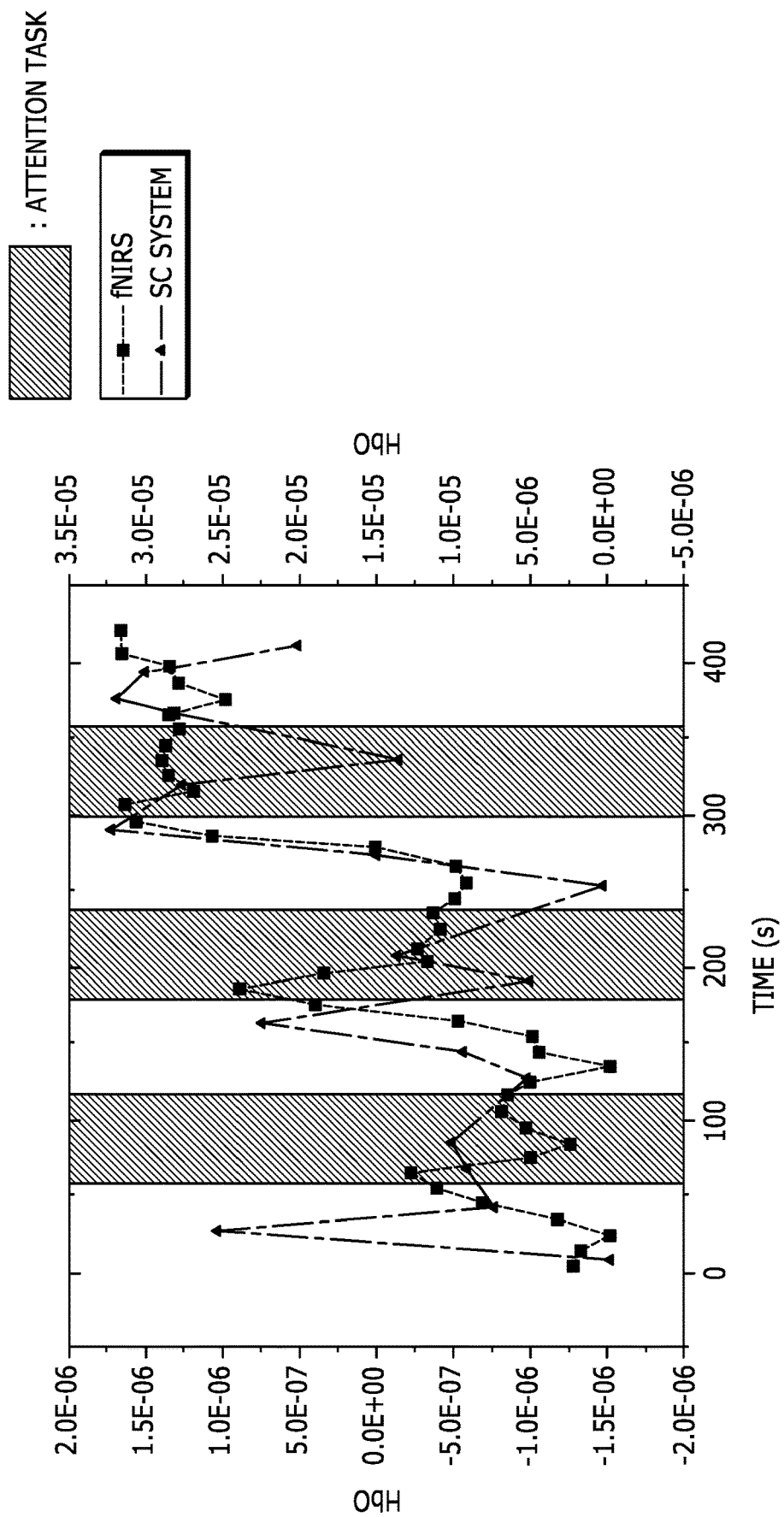
FIG. 14 illustrates HbO comparison for fNIRS and SCL system measurements according to the attention test of FIGS. 13A and 13B.

First, it was verified that the fNIRS and SCL systems showed good correlation for HbO. FIG. 14 illustrates the HbO comparison for the two system, where the solid curve represents the measurement from the fNIRS system, and the dotted curve represents measurements from the SCL system, with the shaded regions corresponded to the period of the attention test. It was found that that the HbO behavior for the two systems track each other and demonstrate an expected pattern. The slight phase shift between the two curves may result from the SCL system being controlled separately from the fNIRS system, which may introduce unintentional delay.

Figures 15, 16:
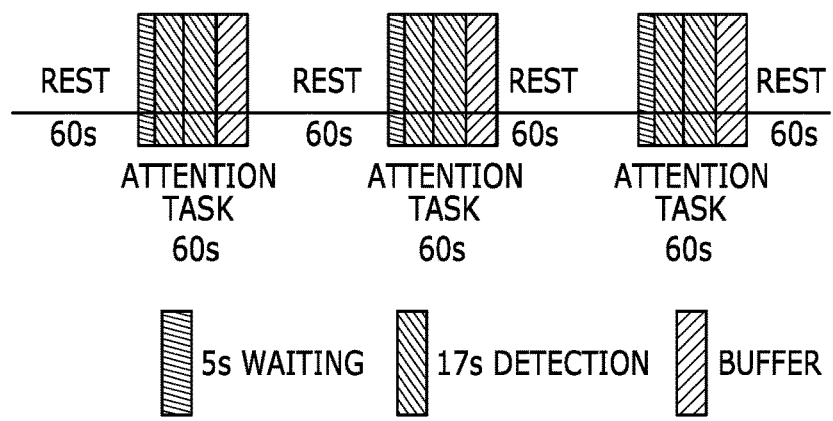
FIG. 15 illustrates the cognitive attention measurement protocol used for a second cognitive attention test.
FIG. 16 is a table of the results of applying the "best of 6" screening method after the outliers are removed from the results of the second attention test of FIG. 15.

Cognitive Attention Test Example: An example SCL system was further used to assess HbO, HbR, and CCO correlations during a second cognitive attention test. In this example, the same CCO probe 1200 of FIG. 12A was used, in the SCL system 500 of FIG. 5A. The experiment was performed using a pilot human study involving 25 healthy participants. FIG. 15 illustrates the cognitive attention test protocol used for the second cognitive attention test.

Some implementations of the SCL systems described herein use an earlier prototype with a slower collection speed of around ~17 sec per scan, referred to herein as an overall data acquisition time. The slower overall data acquisition, in some examples, could allow for the SCL system to experience motion artifacts and other environmental fluctuations within the scan time, affecting the captured data taken during the measurement. More specifically the SCL system 500 configuration of FIG. 5A, with a 17 seconds per wavelength scan timing, in the scanning wavelength range of 750 nm to 900 nm, the SCL system 500 would take 50 data points in 3 nm steps. Since it takes approximately 100 ms for the grating in the spectrometer to move to a particular wavelength step, and since the data point acquisition time was about 100 ms once at that step (e.g., due to waiting for the lock-in amplifier to settle, read the output value, etc.), about 50 data points multiplied by 200 ms per point corresponded to 10 sec of scanning time. It takes 7 addition seconds for initialization of the instrument and moving the grating back to the starting position. The long data acquisition time was due to the particular scanning spectrometer used. Subsequent iterations of the of the SCL system include an acousto-optic tunable filter that reduced the overall data acquisition time from 17 s to approximately 0.5 s.

FIG. 15 illustrates the detection time relative to the second attention test protocol, for the example experiment herein. For the protocol, the attention task period was 60 sec, where it took about 5 seconds for the human participant to respond. As a result, our detection begins about 5 seconds after the start of the attention task, leaving about 55 seconds in which to conduct measurements. In principle, we should be able to fit 3 of the 17 second scans within the 55 second measurement time. However, because of some timing inaccuracy in starting and stopping as well as other timing jitters, we take only two scans per attention task period, so that we avoid obtaining only a partial scan or a scan that overlaps the attention period and the rest period.

Slow data acquisition or scan time can lead to data corruption due to motion artifacts, environmental changes, and other fluctuations within the 17 second scan time. For example, if the participant moves within the 17 seconds, a fairly common occurrence, some example SCL systems would not distinguish changes in the hemodynamic or CCO signal from the motion artifact. As a consequence of this timing difference, the SCL system used for this experiment was configured such that not all blocks of data collected with the SCL system were treated as accurate. Instead, a screening filter was applied to the data collected on the 25 participants to determine which data sets to accept and which ones to discard. A number of different filter techniques are described herein, including, using signal threshold values for CCO signals and filtering out signals before the threshold. Filtering can be based on other statistical relevance measurements, such as based on data within or outside a standard deviation of the mean. Filtering can be based on skew of the CCO signal data. In some examples, filtering can be random, where random measured CCO signals are selected from a set of collected CCO signals. In some examples, CCO signal values are filtered based on measured HbO and/or HbR values and whether these values are above a respective threshold. In some examples, CCO signal values are filtered based on whether the SNR of the CCO signal values is within a predetermined range or whether the comparative SNR of the CCO signal to one of both of the HbO and HbR signals is within a predetermined range. Another example filtering would include using an accelerometer to measure movement, and then removing CCO, HbO, and HbR data exhibiting too much movement. In yet another example, a camera can be used to see capture images or video and assess if there is movement, and remove captured data corresponding to those movement times.

For the second attention experiment, the CCO signal data was filtered based on the HbO observation. That is, in some examples, the SCL system is configured to filter CCO signal data representative of metabolic state, based on oxygenation data, such as HbO and/or HbR data. During the current attention test, for example, the activity was expected to require more brain function and brain metabolism, and a consequent increase in the oxygen sent to the brain (e.g., increase in HbO) was expected. As a result, a two-step filtration was conducted in the screening of the data. First, data was discarded from "outlier" participants. Three types of outliers were identified, which led to discarding of the data from 8 participants. Of the 8 participants, there were technical errors in data acquisition during two of the participants' measurements; hence, the data from these two participants was discarded. Three additional participants were removed due to unsatisfactory signal quality, which was believed to be due to significant motion artifacts. In this example, unsatisfactory signal quality was defined as having an SNR of the ratio between two adjacent measurements that is more than three standard deviations from the mean. Finally, yet another three participants had more than 3 out of 9 data blocks with HbO concentration lower than the baseline, and they were discarded because of the expected increasing HbO during attention blocks, as establish by prior research. All of the eight participants discarded were likely due to improper placement of the probe, motion artifacts, or other environmental fluctuations leading to data errors.

After removing the outliers, 17 out of 25 participants' data remained. A second, further filtering was then applied to the remaining data, which is described in more detail below. Two filtering methods were used to remove artifacts that may be related to motion during the data acquisition time. Both filtering methods provide comparable results and support the following hypothesis: during the attention task, although the HbO concentration increases, the redox state of CCO decreases. It is noteworthy that HbO and CCO are not always anti-correlated when measured on other parts of the body. For example, in the blood pressure test previously discussed, CCO was more or less constant while the HbO increased initially, as observed in FIG. 8.

Figure 17:
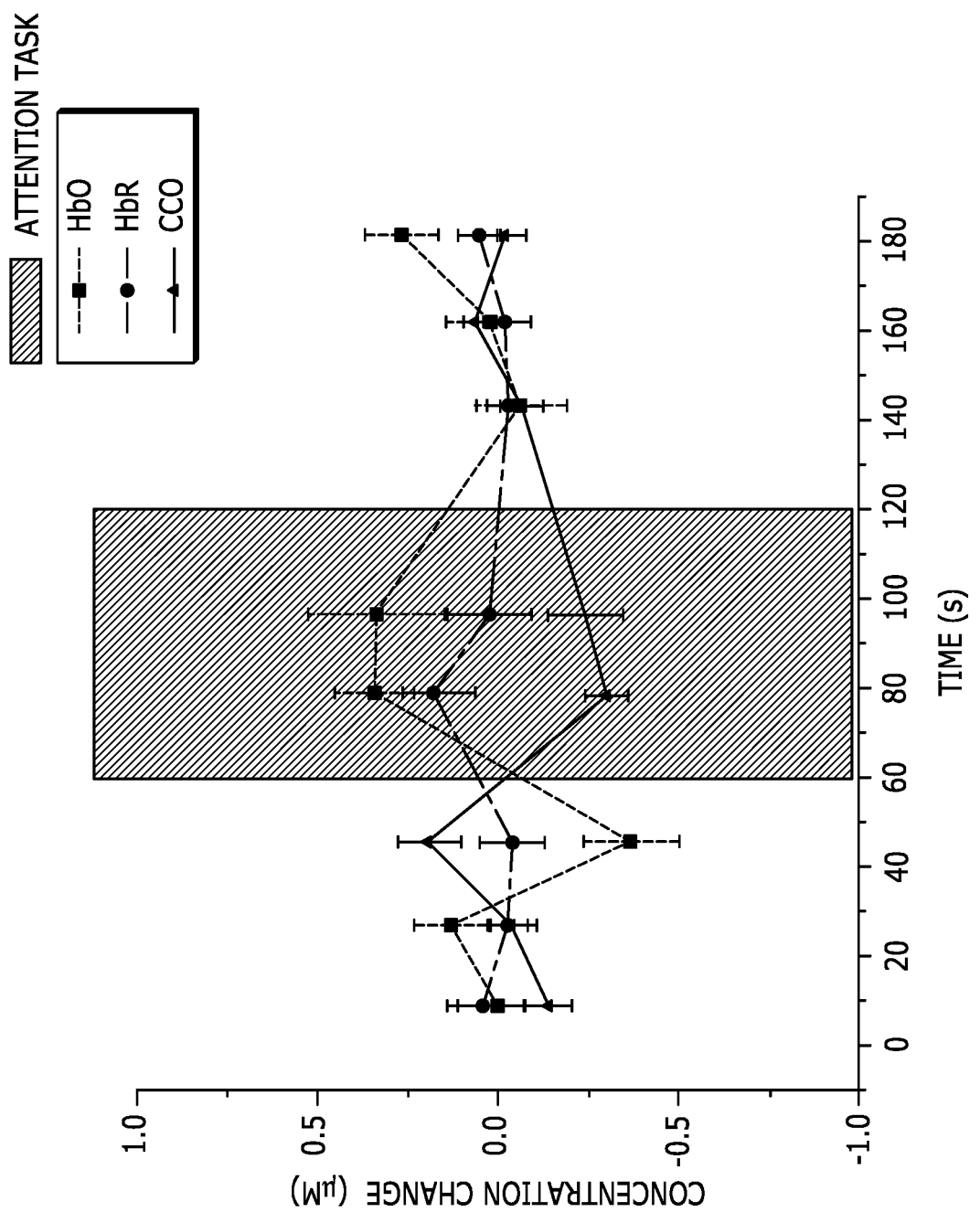
FIG. 17 illustrates a change in HbO, HbR, and the redox state of CCO after applying a "best of 6" screening.

Best of 6 data screening method: In the second data screening step, the SCL system did not accept all 9 blocks of attention test data for the 17 participants remaining after removing the outliers. To further remove data affected by motion artifacts, one of two second screening methods was used in the SCL system 500. The first method is called "best of 6" approach. In this implementation, the SCL system 500 would example CCO signal data, and out of the nine blocks of data per participant, only use the six data blocks with the largest increase in HbO concentration during the attention test compared to the resting period. The table in FIG. 16 shows the results of applying the best of 6 screening method after the outliers are removed. The first column indicates the participant number, and the second column shows out of the 6 blocks per participant how many have decreasing CCO levels. In particular, with the "best of 6" method about 67% of the time (e.g., 68 blocks out of 6×17=102) the CCO decreases while the HbO increases. FIG. 17 illustrates the change in HbO, HbR, and the redox state of CCO after applying the "best of 6" screening. The lines show the average values, while the error bars indicate the standard error. During the attention test period, the HbO on average increases while the redox state of CCO on average decreases. The HbR is more unpredictable, but this may be because HbR is generally harder to measure and has a lower signal to noise ratio in the measurement. While a "best of 6" filtering method was used in the above example, any number of data blocks or data sets may be used in a "best of n" filtering method with "n" being the number of data blocks to be used for further analysis.

HbO increasing screening method: As an alternative second screening method, the example SCL system 500 was configured to apply an "HbO increasing" process after removing the outlier participants in the first screening step. This alternative second screening yielded approximately the same results of HbO increasing and the redox state of CCO decreasing during the attention test, although with a larger contrast for the CCO change and HbO change. As before, the first step was to exclude the outlier participants, leaving a set of 17 participants to work from (9 blocks of data per participant). Next, out of the nine blocks, the blocks were selected for the "HbO increasing" when during the attention test the HbO level is higher than that of the resting state. The table in FIG. 18 illustrates the resulting data selection. The first column is the participant number, and the second column provides the number of data blocks (out of nine) that have HbO increasing. For example, out of the total of 9 blocks×17 participants=153 data blocks, 72 data blocks (72/153=47%) have the HbO increasing during the attention test. Since this is the expected behavior, with the "HbO increasing" criteria we only use these 72 data blocks. Finally, the third column in FIG. 18 shows out of the 72 data blocks with HbO increasing, how many of the data blocks show the redox state of CCO decreasing. In particular, 57/72=79.2% of the accepted data blocks show that CCO decreases while HbO increases during the attention test. In examples, other screening methods as the second screening method, or in series with the previously described screening methods, to further filter the data. Some example potential screening methods include an HbO decreasing filtration (i.e., when the HbO during a test is lower than that of a resting state), HbR increasing filtration (i.e., when the HbR during a test is higher than that of a resting state), HbR decreasing filtration (i.e., when the HbR during a test is lower than that of a resting state), a CCO increasing filtration (i.e., when the CCO during a test is higher than that of a resting state), and a CCO decreasing filtration (i.e., when the CCO during a test is lower than that of a resting state).

Figure 19:
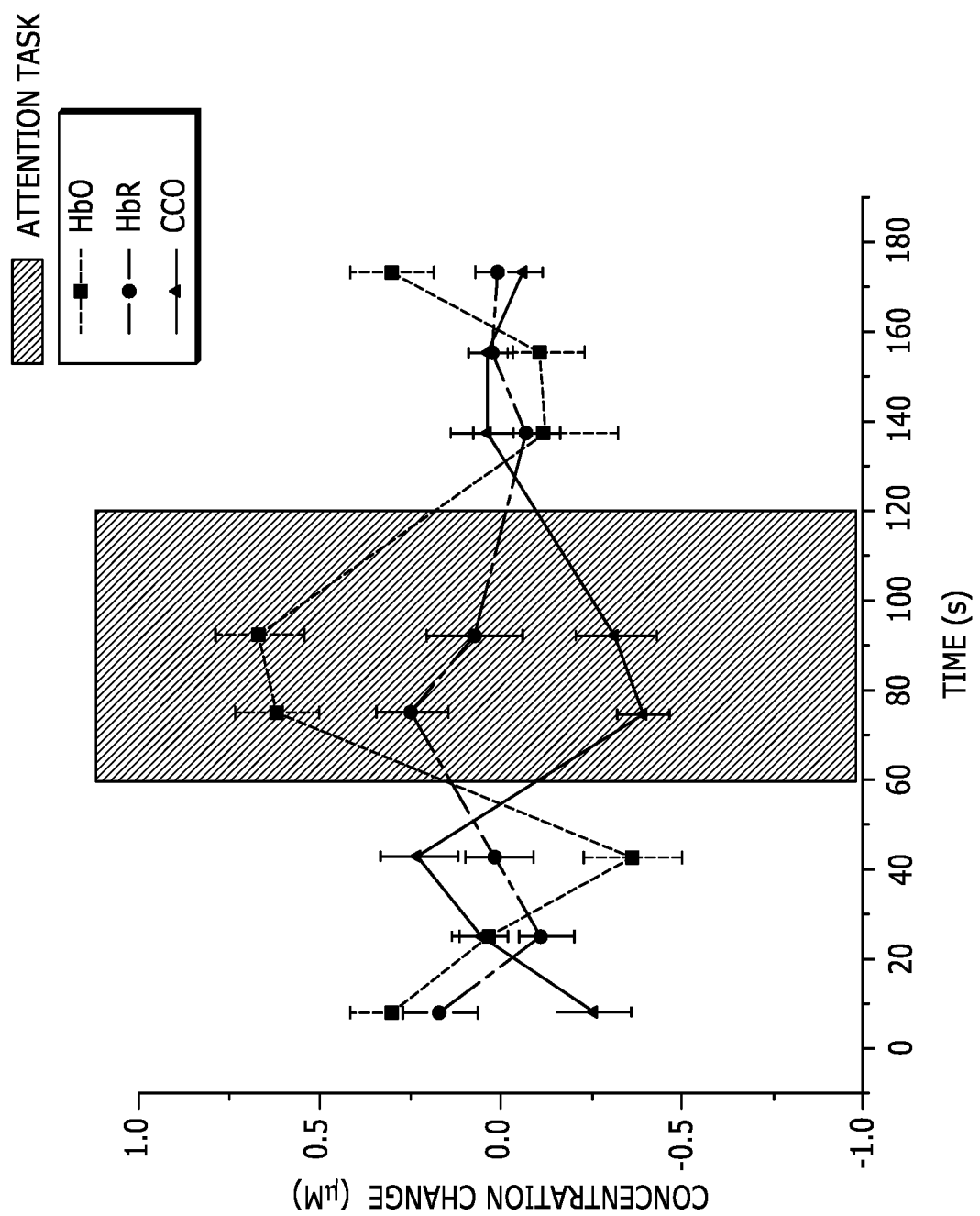
FIG. 19 is a plot of the change in HbO, HbR and the redox state of CCO during the attention test for an "HbO increasing" data selection.

FIG. 19 is a plot of the change in HbO, HbR and the redox state of CCO during the attention test for the "HbO increasing" data selection method described above. The lines correspond to the average of the data, while the bars indicate the variance on the measurements. As in the previous analysis, it was found that the HbO increases during the attention test and the CCO decreases. With the HbO screening method, the amount of concentration change is larger, but the results are consistent with the "best of 6" approach. As before, the HbR does not show a clear trend, which may be due to the difficulty in measuring HbR.

Based on the cognitive attention test results, two questions were further examined, the two questions related to the new correlations between CCO and HbO/HbR determined from our tests. First, why does the redox state of CCO decrease during the attention test, and second, how do the results compare with the literature? It is shown below that the redox state of CCO decreasing is consistent with models on CCO in cell metabolism, and that the results shown are more definite than other published results because of a higher signal-to-noise ratio due to a number of factors in the described experimental set-up. As mentioned above, referring to "CCO measurements" means measuring the changes in the redox state of CCO. CCO exists in two states: oxidized CCO and reduced CCO, the sum of which is a constant. The redox state of CCO is defined as the ratio of oxidized CCO and reduced CCO.

Figure 20:
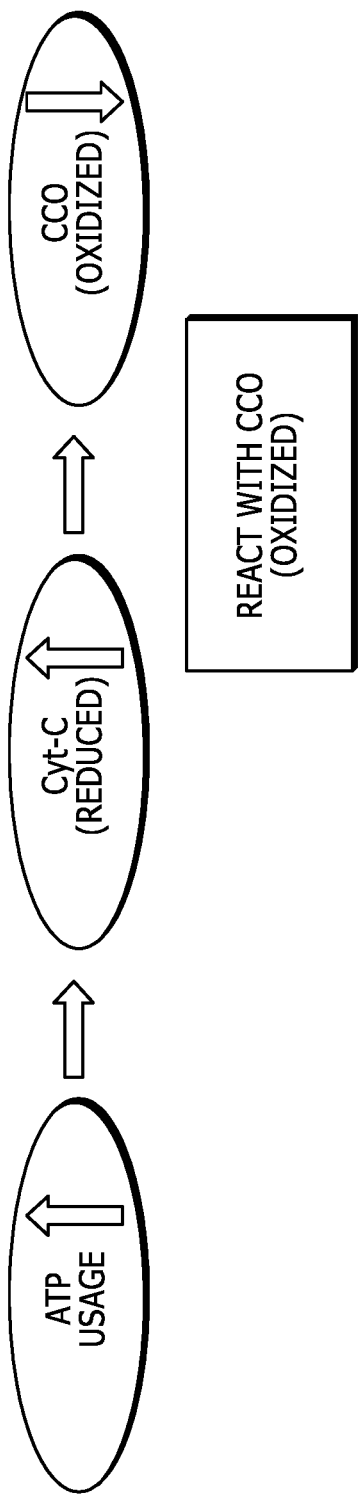
FIG. 20 is a block diagram illustrating the resultant trends between CCO redox state, cellular ATP demand, and hydrolysis rate.

In the cognitive attention tests described above, it was observed that the level of oxidized CCO decreases, and thus the reduced level increases, during the attention test and that the CCO redox state returns to resting levels during the recovery period. These observations are consistent with the interpretation of CCO redox state as an indicator of cellular ATP demand and hydrolysis rate. FIG. 20 is a block diagram illustrating the resultant trends between the CCO redox state, cellular ATP demand, and hydrolysis rate described. Levels of reduced cytochrome c, which is the substrate and electron donor for the CCO reaction, increase with increasing ATP hydrolysis2. The CCO enzyme becomes increasingly reduced as cytochrome c becomes increasingly reduced with increasing rates of metabolic ATP use and demand. The paradoxical increase in oxygenation that occurs concurrently with increased metabolic ATP use during the attention test protocol is observed in BOLD imaging (Emir, U. E., Ozturk, C., & Akin, A., "Multimodal investigation of fMRI and fNIRS derived breath hold BOLD signals with an expanded balloon model," Physiological measurement, 29(1), 49 (2007)) and is understood to be associated with a hyperemic response to local metabolic demand. Thus, the disclosed observations are consistent with the expected physiological response in local oxygenation while providing the first non-invasive simultaneous measurements of both cerebral oxygenation and metabolic demand using an optical sensor.

Another explanation for the presented experimental cognitive attention test results is as follows. When the attention test begins, the frontal lobe part of the brain, which controls important cognitive skills in humans, becomes more active, as compared to a baseline or rest state). The more active frontal lobe requires more oxygen to operate, and the circulatory system of the human responds by delivering more oxygenated hemoglobin (HbO) to the frontal lobe. Hence, during the attention test there is an increase in the HbO level as provided by the blood transport system. The more active frontal lobe also requires more energy (ATP) to operate. As discussed above, levels of reduced cytochrome c (cyt-c) increases as the ATP usage increases, which in turn causes more oxidized CCO enzyme to become reduced. Therefore, in the measurements of CCO, a decreased level of oxidized CCO is observed during the attention tasks (FIG. 20).

The conceptual picture can also be used to understand the other experiments described in this paper. For the blood pressure test (e.g., applying >100 mm Hg pressure for ~4 minutes and measuring with the probe on the forearm), it was found, as shown in FIG. 8, that the CCO level does not change substantially from the baseline. This is reasonable, because even when applying pressure to the upper arm the muscles are not working in the forearm, so they do not need additional energy or an increased rate of metabolism.

In the breath holding test (e.g., holding breath for ~30 seconds, and then breathing normally for ~5 minutes and measuring with the probe on the forehead), it was found, as shown in FIGS. 10 and 11A, that the HbO increases during the breath holding period. Also, as shown in FIG. 11B, it was found that during the breath holding period that the redox state of CCO decreases generally. These results are consistent with the following picture of the brain operation. First, the brain is a protected organ, so when the breath is held, the "fight-or-flight" response activates to help the brain. Second, when humans voluntarily withhold their breath, brain signals nevertheless are sent to tell the body to breath. These signals continue through central respiratory rhythm that appears to take place throughout breath holding. Thus, in response to the breath holding, the brain is put in alert mode and becomes more active, thereby requiring more energy and leading to a decrease in the CCO level. The level of CCO is further reduced as brain activity continues but the supply of oxygen, and therefore oxygenated CCO, dwindles. Without an adequate supply of oxygen to regenerate oxidated CCO more of it remains in the reduced state. Together these two events decrease CCO and eventually trigger the involuntary cessation of the voluntary breath holding before the brain experiences a critically low supply of energy. Deviations of expected CCO, HbO, and HbR trends and correlations provide insight into abnormal brain metabolism and functionality and may assist in diagnosing conditions. For example, increasing HbO indicates more oxygenated blood flow to a region of tissue, and a simultaneously constant CCO reading indicates that brain tissue is not functioning, and may be helpful in diagnosing a concussion or other brain abnormality. All of the experiments described highlight that the hemodynamic response is related to the transport of oxygen by the circulatory system, while the CCO measurements provide insight into the metabolism or energy use and energy reserves in the organ.

The various tests and measurements described above were performed according to measurement protocols designed to achieve the goals of the measurement of test. Each of the protocols includes one or more of an overall measurement time, various measurement periods within the overall measurement time with each period denoting a different circumstance or action being performed, various actions to be performed, environmental conditions, specific stimuli applied and/or provided to a subject or individual, or another parameter or measure for performing a measurement or test. For example, the breath holding test described above includes 30 second periods of breath holding, followed by 5 minute periods of normal breathing, performed multiple times. Overall measurement times may span seconds, minutes, hours, or even days. For example, the overall measurement time may be hours or days for a patient that requires constant monitoring of brain functionality and metabolism during operation, or to observe improved brain functionality and/or metabolism during a treatment. The stimuli applied and/or provided to the subject may include one or more images, a hearing/sound stimuli, tactile external stimuli, one or more gaseous chemicals, an electrical stimuli, one more substances provided intravenously, or another stimuli for performing testing and/or monitoring of brain functionality and metabolism.

Previously published results also studied the attention test in humans (e.g., Kolyva, C., Tachtsidis, I., Ghosh, A., Moroz, T., Cooper, C. E., Smith, M., & Elwell, C. E., "Systematic investigation of changes in oxidized cerebral cytochrome c oxidase concentration during frontal lobe activation in healthy adults," Biomedical optics express, 3(10), 2550-2566 (2012)), but the CCO measurements in the study were inconsistent or inconclusive. On the other hand, with the example SCL system of the present techniques, it is herein demonstrated, results that are more definitive, and namely that HbO increases and CCO decreases during the attention. The results presented herein are more conclusive, in part, because the SCL systems described are able to measure CCO with a much higher signal-to-noise ratio (SNR). There are several design reasons for the higher SNR. First, the reference conventional test uses a lamp, while the SCL systems described use a super-continuum laser as a light source. This results in nearly an order-of-magnitude (or greater) increase in the signal brightness, and, hence, an improvement to the SNR. Moreover, the SCL system 500 configuration in FIG. 5A, for example, has a number of particular attributes that increase the SNR. The SCL system 500 of FIG. 5A employs a reference arm to divide out any laser or environmental fluctuations or variations, which is particularly important when using a super-continuum laser that has intensity fluctuations in shorter wavelengths. It was also found that it was important to use a polarizer before splitting the beam, because varying polarization state can lead to fluctuations due to polarization dependent components in the apparatus. In addition, by using the lock-in amplifiers 530, the SCL system 500 was also able to increase the SNR because the system 500 can block out ambient light as well as other stray signals; namely, the lock-in amplifier 530 significantly attenuates signals that are not at the chopper 504 frequency. Further still, the SCL system 500 is adaptive and tunable for higher performance. As discussed, the SNR and tolerance to motion artifacts can also be further improved in the SCL system 500 configuration of FIG. 5A by using a faster tunable filter (e.g., an acousto-optic tunable filter) in place of a scanning grating spectrometer as the spectrometer 507.

In summary, for the cognitive attention test, a pilot human study of 25 participants was conducted using a cognitive attention test in combination with principled physiological validations of the technology such as blood pressure and breath-holding approaches. The results show that during the attention task, the level of HbO increases and the level of oxidized CCO decreases. The measured behavior is consistent with prior studies showing an increase in HbO in the frontal lobe during attention tasks and the interpretation of the CCO redox state as an indicator of cellular ATP demand and metabolism in the active brain region. Thus, the described measurements provide a non-invasive, simultaneous measurement of both cerebral hemodynamic response and metabolic demand using an optical sensor.

More generally, in various examples, the SCL systems herein provide a non-invasive tool for monitoring changes in metabolism as well as hemodynamic response. Using the all-fiber-integrated SCL as the key enabling technology, the SCL systems herein can provide a practical, cost-effective, portable, non-invasive means of monitoring brain and organ oxygenation and metabolism in the emergency department, operating room, or other medical facilities. Applications of the SCL system range from a new tool for screening concussion patients to use in an intensive care unit to gauge patient's organ response to treatments, guide resuscitation, and provide information about potential future clinical courses of action.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the target matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled,"

however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. An apparatus for measuring hemodynamic or metabolic function of an organ or tissue region of a subject, the apparatus comprising:
    a super-continuum laser configured to generate a pulsed super-continuum emission, the emission having a wavelength range coinciding with at least one of a near infrared (NIR) wavelength range and a short-wave infrared (SWIR) wavelength range, the super-continuum laser having a multi-stage configuration formed of a fiber pre-amplifier stage feeding an optical noise filtering stage feeding a fiber amplifier stage for generating the pulsed super-continuum emission;
    a probe having a probe housing fixedly connected to a source fiber configured to receive the pulsed super-continuum emission from the fiber amplifier stage, the probe housing further fixedly connected to a collection fiber configured to receive reflected emission from the organ or tissue region, wherein the probe is configured to apply, via the source fiber, the super-continuum emission to the organ or tissue region of the subject, the probe further configured to receive the reflected emission from the organ or tissue region via the collection fiber;
    a detector configured to detect the reflected emission and further configured to generate a signal indicative of the detected reflected emission,
        wherein the detector has a dual-arm differential measurement configuration configured to improve a signal-to-noise ratio of the signal, the dual-arm differential measurement configuration includes a beam splitter configured to separate the pulsed super-continuum emission into a sample arm beam and a reference arm beam, and
        wherein the dual-arm differential measurement configuration is configured to provide (i) the sample arm beam to the detector and (ii) the reference arm beam to a reference detector configured to generate another signal indicative of the detected reference arm beam; and
    a processor configured to execute machine readable instructions that, when executed, cause the processor to:
        determine, from the signal indicative of the reflected emission, a simultaneous (i) metabolic state of the organ or tissue region from a metabolic chromophore and (ii) an oxygenation state of the organ or tissue region from at least one oxygenation chromophore;
    wherein the signal-to-noise ratio is further improved using a lock-in amplifier or a polarizer; and
    wherein the machine readable instructions, when executed, further cause the processor to:
        compare the metabolic state of the organ or tissue region with the oxygenation state of the organ or tissue region; and
        identify an organ or tissue functionality of the subject from the comparison of the metabolic state and the oxygenation state of the organ or tissue region.

2. The apparatus of claim 1, wherein the machine readable instructions further cause the processor to:
    compare the metabolic state to a previous metabolic state of the organ or tissue region
    and determine, from the comparison of the metabolic state and previous metabolic state, a trend of the metabolic state;
    compare the oxygenation state to a previous oxygenation state of the organ or tissue region and determining, from the comparison oxygenation state and the previous oxygenation state, a trend of the oxygenation state;
    determine a correlation between the trend of the metabolic state and the trend of the oxygenation state; and
    identify the organ or tissue functionality of the subject from the determined correlation.

3. The apparatus of claim 1, wherein the organ or tissue functionality is selected from the group consisting of ischemia, hemorrhage, hypoxia, encephalopathy, concussion, tumor, shock, trauma, stroke, infection, infarction, and cardiopulmonary disease.

4. The apparatus of claim 1, wherein the metabolic chromophore comprises Cytochrome-C-Oxidase (CCO) and the at least one oxygenation chromophore comprises oxygenated hemoglobin (HbO) or deoxygenated (HbR) hemoglobin.

5. The apparatus of claim 1, wherein the machine readable instructions further cause the processor to (i) apply the identified organ or tissue functionality to screening the subject, (ii) apply the identified organ or tissue functionality to gauge one or more organ or tissue responses to treatments, (iii) provide information about future clinical courses of action, (iv) apply the identified organ or tissue functionality to guide resuscitation, wherein to identify the tissue or organ functionality, the apparatus is deployed in one of prehospital settings, emergency rooms, inpatient and outpatient environments, or an operating room.

6. An apparatus for measuring hemodynamic or metabolic function of an organ or tissue region of a subject, the apparatus comprising:
    a super-continuum laser configured to generate a pulsed super-continuum emission, the emission having a wavelength range coinciding with at least one of a near infrared (NIR) wavelength range and a short-wave infrared (SWIR) wavelength range, the fiber super-continuum laser having a multi-stage configuration formed of a fiber pre-amplifier stage feeding an optical noise filtering stage feeding a fiber amplifier stage generating the pulsed super-continuum emission;
    a probe having a probe housing fixedly connected to a source fiber configured to receive the pulsed super-continuum emission from the fiber amplifier stage, the probe housing further fixedly connected to a collection fiber configured to receive reflected emission from the organ or tissue region, wherein the probe is configured to apply via the source fiber the super-continuum emission to the organ or tissue region of the subject, the probe further configured to receive the reflected emission from the organ or tissue region via the collection fiber;

a detector configured to detect the reflected emission and further configured to generate a signal indicative of the detected reflected emission, wherein the detector has a dual-arm differential measurement configuration configured to improve a signal-to-noise ratio of the signal, the dual-arm differential measurement configuration includes a beam splitter configured to separate the pulsed super-continuum emission into a sample arm beam and a reference arm beam, and wherein the dual-arm differential measurement configuration is configured to provide (i) the sample arm beam to the detector and (ii) the reference arm beam to a reference detector configured to generate another signal indicative of the detected reference arm beam; and a processor configured to execute machine readable instructions that, when executed, cause the processor to:

determine, from the signal indicative of the reflected emission, a (i) metabolic state of the organ or tissue region from a metabolic chromophore or (ii) an oxygenation state of the organ or tissue region from at least one oxygenation chromophore;

identify, from the metabolic state or the oxygenation state, an organ or tissue functionality; and provide an output indicative of the organ or tissue functionality.

7. The apparatus of claim 6, wherein the metabolic chromophore comprises Cytochrome-C-Oxidase (CCO) and the at least one oxygenation chromophore comprises oxygenated hemoglobin (HbO) or deoxygenated (HbR) hemoglobin.

8. The apparatus of claim 6, wherein the machine readable instructions further cause the processor to:

compare the metabolic state to a previous metabolic state of the organ or tissue region
and determine, from the comparison of the metabolic state and previous metabolic state, a trend of the metabolic state;

compare the oxygenation state to a previous oxygenation state of the organ or tissue region and determining, from the comparison oxygenation state and the previous oxygenation state, a trend of the oxygenation state;

determine a correlation between the trend of the metabolic state and the trend of the oxygenation state; and identify the organ or tissue functionality of the subject from the determined correlation.

9. The apparatus of claim 6, wherein the organ or tissue functionality is selected from the group consisting of ischemia, hemorrhage, hypoxia, encephalopathy, concussion, tumor, shock, trauma, stroke, infection, infarction, and cardiopulmonary disease.

10. The apparatus of claim 6, wherein a signal-to-noise ratio of the signal is improved by using a dual-arm differential measurement technique including a beam splitter configured to separate the pulsed super-continuum emission to generate a sample arm beam and a reference arm beam, wherein the sample arm beam is provided to the probe and the reference arm beam is provided to a reference detector configured to generate another signal indicative of the detected reference arm beam;

wherein the signal-to-noise ratio is further improved using a lock-in technique or a polarizer; and wherein the machine readable instructions further cause the processor to:

compare the data of the another signal indicative of the reference arm beam with the signal indicative of the reflected emission.

11. The apparatus of claim 6, wherein the machine readable instructions further cause the processor to (i) apply the identified organ or tissue functionality to screening the subject, (ii) apply the identified organ or tissue functionality to gauge one or more organ or tissue responses to treatments, (iii) provide information about future clinical courses of action, (iv) apply the identified organ or tissue functionality to guide resuscitation, wherein to identify the tissue or organ functionality, the apparatus is deployed in one of prehospital settings, emergency rooms, inpatient and outpatient environments, or an operating room.

12. The apparatus of claim 6, wherein to identify a tissue or organ functionality, the apparatus identifies the tissue or organ functionality during surgery, during a medically induced coma, during sedation, during treating neonates, during injury therapy, or to guide treatments in settings selected from the group consisting of prehospital settings, emergency rooms, inpatient and outpatient environments, and an operating room.

13. The apparatus of claim 6, wherein the source fiber comprises a bundle with a plurality of fibers, and the collection fiber comprises a second bundle with another plurality of fibers.

14. An apparatus for measuring hemodynamic or metabolic function of one or more organ or tissue regions of a subject, the apparatus comprising:

a super-continuum laser configured to generate a pulsed super-continuum emission, the emission having a wavelength range coinciding with at least one of a near infrared (NIR) wavelength range and a short-wave infrared (SWIR) wavelength range;

a probe having a probe housing fixedly connected to a source fiber bundle comprising a plurality of source fibers configured to receive the pulsed super-continuum emission from the super-continuum laser, the probe housing further coupled to a collection fiber bundle comprising a plurality of collection fibers configured to receive reflected emission from a tissue region, wherein the probe is configured to apply via one or more of the source fibers the super-continuum emission to the one or more organ or tissue regions of the subject, wherein the one or more organ or tissue regions comprise a forehead, temple, scalp, forearm, leg, chest or another body part of the subject, and the probe further configured to receive the reflected emission from the one or more organ or tissue regions via one or more of the collection fibers;

one or more detectors configured to detect the reflected emission and further configured to generate one or more signals indicative of the detected reflected emission, wherein the detector has a dual-arm differential measurement configuration configured to improve a signal-to-noise ratio of the signal, the dual-arm differential measurement configuration includes a beam splitter configured to separate the pulsed super-continuum emission into a sample arm beam and a reference arm beam, and wherein the dual-arm differential measurement configuration is configured to provide (i) the sample arm beam to the detector and (ii) the reference arm beam to a reference detector configured to generate another signal indicative of the detected reference arm beam; and a processor configured to execute machine readable instructions that, when executed, cause the processor to:
- determine, from the one or more signals indicative of the detected reflected emission, (i) a metabolic state of the one or more organ or tissue regions from a metabolic chromophore and (ii) an oxygenation state of the one or more organ or tissue regions from at least one oxygenation chromophore; and
- compare the metabolic state to a previous metabolic state of the one or more organ or tissue regions and determine, from the comparison of the metabolic state and previous metabolic state, a trend of the metabolic state;
- compare the oxygenation state to a previous oxygenation state of the one or more organ or tissue regions and determine, from the comparison oxygenation state and the previous oxygenation state, a trend of the oxygenation state;
- determine a correlation between the trend of the metabolic state and the trend of the oxygenation state; and
- identify an organ or tissue functionality of the subject from the determined correlation.

15. The apparatus of claim 14, wherein the metabolic chromophore comprises Cytochrome-C-Oxidase (CCO) and the at least one oxygenation chromophore comprises oxygenated hemoglobin (HbO) or deoxygenated (HbR) hemoglobin.

16. The apparatus of claim 14, wherein the machine readable instructions further cause the processor to (i) apply the identified organ or tissue functionality to screening the subject, (ii) apply the identified organ or tissue functionality to gauge one or more organ or tissue responses to treatments, (iii) provide information about future clinical courses of action, (iv) apply the identified organ or tissue functionality to guide resuscitation, wherein to identify the tissue or organ functionality, the apparatus is deployed in one of prehospital settings, emergency rooms, inpatient and outpatient environments, or an operating room.

17. The apparatus of claim 14, wherein the organ or tissue functionality is selected from the group consisting of ischemia, hemorrhage, hypoxia, encephalopathy, concussion, tumor, shock, trauma, stroke, infection, infarction, and cardiopulmonary disease.

18. The apparatus of claim 14, wherein a signal-to-noise ratio of the one or more signals is improved by using a dual-arm differential measurement technique comprising a beam splitter configured to separate the pulsed super-continuum emission to generate a sample arm beam and a reference arm beam, wherein the sample arm beam is provided to the probe and the reference arm beam is provided to a reference detector configured to generate another signal indicative of the detected reference arm beam;
- wherein the signal-to-noise ratio is further improved using a lock-in technique or a polarizer; and
- wherein the machine readable instructions further cause the processor to:
  - compare the data of the another signal indicative of the reference arm beam with the one or more signals indicative of the reflected emission.

19. The apparatus of claim 14, further comprising:
- a wavelength filter configured to filter the emission to a desired set of wavelengths, wherein the wavelength filter is a tunable optical filter or an acousto-optic tunable filter;
- an optical chopper or modulator configured to modulate the amplitude of the emission to generate emission pulses; and
- wherein the wavelength range is approximately 750 nanometers to 900 nanometers.

20. The apparatus of claim 14, wherein to identify a tissue or organ functionality, the apparatus identifies the tissue or organ functionality during surgery, during a medically induced coma, during sedation, during treating neonates, during injury therapy, or to guide treatments in settings selected from the group consisting of prehospital settings, emergency rooms, inpatient and outpatient environments, and an operating room.

* * * * *